(12) United States Patent
Huang et al.

(10) Patent No.: US 9,222,093 B2
(45) Date of Patent: Dec. 29, 2015

(54) TWO-WAY, PORTABLE RIBOSWITCH MEDIATED GENE EXPRESSION CONTROL DEVICE

(75) Inventors: Jian-Dong Huang, Hong Kong (CN); Ye Jin, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 675 days.

(21) Appl. No.: 13/534,774

(22) Filed: Jun. 27, 2012

(65) Prior Publication Data
US 2013/0004980 A1    Jan. 3, 2013

Related U.S. Application Data

(60) Provisional application No. 61/503,453, filed on Jun. 30, 2011.

(51) Int. Cl.
| | | |
|---|---|---|
| C12N 15/113 | (2010.01) | |
| C12N 15/63 | (2006.01) | |
| C12N 15/67 | (2006.01) | |
| C12N 15/72 | (2006.01) | |
| C12N 15/115 | (2010.01) | |

(52) U.S. Cl.
CPC .............. *C12N 15/63* (2013.01); *C12N 15/635* (2013.01); *C12N 15/67* (2013.01); *C12N 15/72* (2013.01); *C12N 15/115* (2013.01); *C12N 2310/16* (2013.01); *C12N 2310/3519* (2013.01); *C12N 2320/10* (2013.01)

(58) Field of Classification Search
None
See application file for complete search history.

(56) References Cited

U.S. PATENT DOCUMENTS 7,563,601 B1    7/2009 Gaur

OTHER PUBLICATIONS

Ellington and Szostak, "In vitro selection of RNA molecules that bind specific ligands", *Nature*, 1990, 346, pp. 818-822.
Tuerk and Gold, "Systematic evolution of ligands by exponential enrichment: RNA ligands to bacteriophage T4 DNA polymerase", *Science*, 1990, 249, pp. 505-510.
Chushak and Stone, "In silico selection of RNA aptamers", *Nucleic Acids Res*, 2009, 37, pp. e87.
Collett et al., "Functional RNA microarrays for high-throughput screening of antiprotein aptamers", *Anal Biochem*, 2005, 338, pp. 113-123.
Li et al., "Fabrication and characterization of RNA aptamer microarrays for the study of protein-aptamer interactions with SPR imaging", *Nucleic Acids Res*, 2006, 34, pp. 6,416-6,424.
Lynch et al., "A high-throughput screen for synthetic riboswitches reveals mechanistic insights into their function", *Chem Biol*, 2007, 14, pp. 173-784.
Lynch and Gallivan, "A flow cytometry-based screen for synthetic riboswitches",*Nucleic Acids Res*, 2009, 37, pp. 184-192.
Muranaka et al., "Mechanism-guided library design and dual genetic selection of synthetic OFF riboswitches", *Chemibiochem*, 2009, 10, pp. 2,375-2,381.
Jin et al., "Use of a riboswitch-controlled conditional hypomorphic mutation to uncover a role for the essential csrA gene in bacterial autoaggregation", *J Biol Chem*, 2009, 284, pp. 28,738-728,745.
Zheng et al., "Identification of the CRP regulon using in vitro and in vivo transcriptional profiling", *Nucleic Acids Res*, 2004, 32, pp. 5,874-5,893.
Grainger et al., "Studies of the distribution of *Escherichia coli* cAMP-receptor protein and RNA polymerase along the *E. coli* chromosome", *Proc Natl Acad Sci USA*, 2005, 102, pp. 17,693-17,698.
Hogema et al., "Catabolite repression by glucose 6-phosphate, gluconate and lactose in *Escherichia coli*", *Mol Microbiol*, 1997, 24, pp. 857-567.
Soutourina et al., "Multiple control of flagellum biosynthesis in *Escherichia coli*: role of H-NS protein and the cyclic AMP-catabolite activator protein complex in transcription of the flhDC master operon", *J Bacteriol*, 1999, 181, pp. 7,500-7,508.
Studier and Moffatt, "Use of bacteriophage T7 RNA polymerase to direct selective high-level expression of cloned genes", *J Mol Biol*, 1986, 189, pp. 113-130.
Luukkonen and Seraphin, "Construction of an in vivo-regulated U6 snRNA transcription unit as a tool to study U6 function", *RNA 4*, 1998, pp. 231-238.
Grilly et al., "A synthetic gene network for tuning protein degradation in *Saccharomyces cerevisiae*", *Mol Syst Biol*, 2007, 3, pp. 127.
Cronin et al., "The lac operator-repressor system is functional in the mouse", *Genes Dev*, 2001, 15, pp. 1,506-1,517.
Ellis et al., "Diversity-based, model-guided construction of synthetic gene networks with predicted functions", *Nat Biotechnol*, 2009, 27, pp. 465-471.
Liu et al., "The RNA molecule CsB binds to the global regulatory protein CsrA and anatagonizes its activity in *Escherichia coli*", *J Biol Chem*, 1997, 272, pp. 17,502-17,510.
Wang et al., "CsrA post-transcriptionally represses pgaABCD, responsible for synthesis of a biofilm polysaccharide adhesion of *Escherichia coli*", *Mol Microbiol*, 2005, 56, pp. 1,648-1,663.
Suess et al., "A theophylline responsive rlboswitch based on helix slipping controls gene expression in vivo", *Nucleic Acids Res*, 2004, 32, pp. 1,610-1,614.
Verhounig et al., "Inducible gene expression from the plastid genome by a synthetic riboswitch", *Proc Natl Acad Sci USA*, 2010, 107, pp. 6,204-6,209.
Win and Smolke, "A modular and extensible RNA-based gene-regulatory platform for engineering cellular function", *Proc Natl Acad Sci USA*, 2007, 104, pp. 14,283-14,288.
Win and Smolke, "Higher-order cellular information processing with synthetic RNA devices", *Science*, 2008, 322, pp. 456-460.

*Primary Examiner* — Antonio Galisteo Gonzalez
(74) *Attorney, Agent, or Firm* — Leason Ellis LLP.

(57) ABSTRACT

A regulatable gene expression construct comprising a nucleic acid molecule comprising a two-way riboswitch operably linked to a target sequence. Also provided is a library screening strategy for efficient creation of target-specific riboswitches. A theophylline-repressible and IPTG-inducible riboswitch device achieves portable control of gene expression control in a 'two-way' manner. The default state of target genes is ON; the targets are switched off by adding theophylline, and switched back to the ON-state by adding IPTG without changing growth medium. The riboswitch device regulates gene expression in a portable, adjustable, and two-way manner with a variety of scientific and biotechnological applications.

4 Claims, 8 Drawing Sheets

SEQUENCE LISTING

<160> NUMBER OF SEQ ID NOS: 14

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ataccagcat cgtcttgatg cccttggcag                                          30

<210> SEQ ID NO 2
<211> LENGTH: 30
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
auaccagcau cgucuugaug cccuuggcag                                      30

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcagacaac gaagtgaaca tcagg                                           25

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggagcactgt attcacagcg ct                                              22

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcctacggg aggcagcag                                                  19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctccgtatta ccgcggctg                                                  19

<210> SEQ ID NO 7
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
auaacuucgu auaguaugc uauacgaagu uau                                   33

<210> SEQ ID NO 8
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
caaacugaaa uaccagcauc gucuugaugc ccuuggcagu ucaaauucag gaugaaugua    60
uuucagggug gugaaugug                                                 79

<210> SEQ ID NO 9
<211> LENGTH: 142
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
caaacugaaa uaccagcauc gucuugaugc ccuuggcagu ucaaauucag gaugaaugua    60
uuucagggug gugaauguga aaccaguaac guuauacgau gucgcagagu augccggugu   120
cucuuaucag accguuuccc gc                                            142

<210> SEQ ID NO 10
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
caaacugaaa uaccagcauc gucuugaugc ccuuggcagu ucaaauucag gaugaacgua    60
uuucagggug gugaaugug                                                 79

<210> SEQ ID NO 11
<211> LENGTH: 116
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11
auaacuucgu auauguaugc uauacgaagu uauuaggucc cucgaagagg ugaaauacca    60
gcaucgucuu gaugcccuug gcaguucacg uauuucaggg uggugaaugu gaaacc       116

<210> SEQ ID NO 12
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caaacugaaa uaccagcauc gucuugaugc ccuuggcagu ucaaauucag gaugaacugg    60
uuucagggug gugaaugug                                                 79

<210> SEQ ID NO 13

```
<211> LENGTH: 94
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
caaacugaaa uaccagcauc gucuugaugc ccuuggcagu ucaaauucag gaugaacugg    60
uuucagggug ggugaaugug aaaccaguaa cguu                                94

<210> SEQ ID NO 14
<211> LENGTH: 61
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gguucacuaa aacaaacuga aauaccaagg caagguauuu caggguggug aaugugaaac    60
c                                                                    61
```

TWO-WAY, PORTABLE RIBOSWITCH MEDIATED GENE EXPRESSION CONTROL DEVICE

CROSS-REFERENCE TO RELATED PATENT APPLICATIONS

This application claims priority to U.S. Provisional Application Ser. No. 61/503,453 filed on Jun. 30, 2011, which is incorporated by reference herein in its entirety.

The instant application contains a Sequence Listing which has been submitted electronically in ASCII format and is hereby incorporated by reference in its entirety. Said ASCII copy, created on Aug. 20, 2015, is named 10030-003025-US1_SL.txt and is 4,190 bytes in size.

1. TECHNICAL FIELD

This invention relates generally to regulation of gene expression. More specifically, the invention relates to RNA regulatory devices that regulate gene expression at both transcriptional and translational levels.

2. BACKGROUND

Gene expression can be effectively regulated by modulating the rate of either transcription of DNA to messenger RNA (mRNA), or translation of the mRNA to the corresponding protein. Many genes include an inducible promoter region that specifically controls expression of the one or more genes operably linked to the promoter region. Transcription of these genes can be turned on or off in response to inducer molecules, including metabolic intermediates, changes in physical conditions including temperature changes, and exogenous molecules such as alcohol, or antibiotics. However, inducible promoters are not available for all physically relevant genes. Consequently, RNA-based gene control elements called riboswitches have attracted increasing attention and artificial riboswitches have been developed for a variety of purposes.

Riboswitches are mRNA-based regulatory devices that mediate ligand-dependent control of gene expression. A riboswitch includes an aptameric region that binds the inducer molecule (ligand), and causes a structural change in the expression platform portion of the mRNA riboswitch that in turn either increases or decreases expression of the corresponding gene. Hence, riboswitches regulate gene expression at the translational level. One example is a theophylline-responsive ON riboswitch for the csrA (carbon storage regulator) gene in *Escherichia coli* which provides flexible control of cellular auto-aggregation and motility of the resulting *E. coli* switch-csrA mutant organism. Riboswitches have also been used to regulate gene expression by mediating pre-mRNA splicing in the presence of an inducer molecule such as theophylline.

Ligand-dependent riboswitches are one-way switches, and, once activated, can be turned off only by removing the riboswitch ligand, rendering them impractical for in vivo applications. For in vitro applications, the growth medium must be diluted or changed to remove the riboswitch ligand. In addition, the riboswitches developed to date are specific to a given target gene and are not applicable to other genes. This lack of portability severely limits the applications suitable for these riboswitches.

It is desirable to obtain a portable riboswitch that provides two-way regulation in response to two distinct ligands. Such a riboswitch could be inserted upstream from the start codon of any target gene and exert two-way control of expression of the gene. Such a device would find a wide variety of applications including scientific studies into gene function, medical applications including gene therapy and applications in biotechnology.

3. SUMMARY

It has been discovered that certain natural mRNAs serve as metabolite-sensitive genetic switches wherein the RNA directly binds a small organic molecule. This binding process changes the conformation of the mRNA, which causes a change in gene expression by a variety of different mechanisms. Modified versions of these natural "riboswitches" (created by using various nucleic acid engineering strategies) can be employed as designer genetic switches that are controlled by specific effector compounds. Such effector compounds that activate a riboswitch are referred to herein as trigger molecules. The natural switches are targets for antibiotics and other small molecule therapies. In addition, the architecture of riboswitches allows actual pieces of the natural switches to be used to construct new non-immunogenic genetic control elements. For example, the aptamer (molecular recognition) domain can be swapped with other non-natural aptamers (or otherwise modified) such that the new recognition domain causes genetic modulation with user-defined effector compounds. The changed switches become part of a therapy regimen-turning on, or off, or regulating protein synthesis. Newly constructed genetic regulation networks can be applied in such areas as living biosensors, metabolic engineering of organisms, and in advanced forms of gene therapy treatments.

Disclosed are isolated and recombinant riboswitches, recombinant constructs containing such riboswitches, heterologous sequences operably linked to such riboswitches, and cells and transgenic organisms harboring such riboswitches, riboswitch recombinant constructs, and riboswitches operably linked to heterologous sequences. The heterologous sequences can be, for example, sequences encoding proteins or peptides of interest, including reporter proteins or peptides. Preferred riboswitches are, or are derived from, naturally occurring riboswitches.

Also disclosed are chimeric riboswitches containing heterologous aptamer domains and expression platform domains. That is, chimeric riboswitches are made up of an aptamer domain from one source and an expression platform domain from another source. The heterologous sources can be from, for example, different specific riboswitches or different classes of riboswitches. The heterologous aptamers can also come from non-riboswitch aptamers. The heterologous expression platform domains can also come from non-riboswitch sources.

Also disclosed are compositions and methods for selecting and identifying compounds that can activate, deactivate or block a riboswitch. Activation of a riboswitch refers to the change in state of the riboswitch upon binding of a trigger molecule. A riboswitch can be activated by compounds other than the trigger molecule and in ways other than binding of a trigger molecule. The term trigger molecule is used herein to refer to molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

Deactivation of a riboswitch refers to the change in state of the riboswitch when the trigger molecule is not bound. A riboswitch can be deactivated by binding of compounds other than the trigger molecule and in ways other than removal of the trigger molecule. Blocking of a riboswitch refers to a condition or state of the riboswitch where the presence of the trigger molecule does not activate the riboswitch. In specific embodiments, the binding of a first ligand to the riboswitch activate the expression of a repressor protein. In turn, activation of the expression of a repressor protein decreases the expression of a target gene. In specific embodiments, the binding of a second ligand to a riboswitch decreases the expression of a repressor protein. In turn, decreased expression of a repressor protein increases the expression of a target gene.

Also disclosed are compounds, and compositions containing such compounds, that can activate, deactivate or block a riboswitch. Also disclosed are compositions and methods for activating, deactivating or blocking a riboswitch. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. A riboswitch can be blocked by, for example, binding of an analog of the trigger molecule that does not activate the riboswitch. In certain embodiments, activation of a riboswitch that controls the expression of a repressor protein decreases the expression of a target gene expression.

Also disclosed are compositions and methods for altering expression of an RNA molecule, or of a gene encoding an RNA molecule, where the RNA molecule includes a riboswitch, by bringing a compound into contact with the RNA molecule. Riboswitches function to control gene expression through the binding or removal of a trigger molecule. Thus, subjecting an RNA molecule of interest that includes a riboswitch to conditions that activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

Also disclosed are compositions and methods for regulating expression of an RNA molecule, or of a gene encoding an RNA molecule, by operably linking a riboswitch to the RNA molecule. A riboswitch can be operably linked to an RNA molecule in any suitable manner, including, for example, by physically joining the riboswitch to the RNA molecule or by engineering nucleic acid encoding the RNA molecule to include and encode the riboswitch such that the RNA produced from the engineered nucleic acid has the riboswitch operably linked to the RNA molecule. Subjecting a riboswitch operably linked to an RNA molecule of interest to conditions that activate, deactivate or block the riboswitch can be used to alter expression of the RNA.

Also disclosed are compositions and methods for regulating expression of a naturally occurring gene or RNA that contains a riboswitch by activating, deactivating or blocking the riboswitch. If the gene is essential for survival of a cell or organism that harbors it, activating, deactivating or blocking the riboswitch can result in death, stasis or debilitation of the cell or organism. For example, activating a naturally occurring riboswitch in a naturally occurring gene that is essential to survival of a microorganism can result in death of the microorganism (if activation of the riboswitch turns off or represses expression). This is one basis for the use of the disclosed compounds and methods for antimicrobial and antibiotic effects.

Also disclosed are compositions and methods for regulating expression of an isolated, engineered or recombinant gene or RNA that contains a riboswitch by activating, deactivating or blocking the riboswitch. The gene or RNA can be engineered or can be recombinant in any manner. For example, the riboswitch and coding region of the RNA can be heterologous, the riboswitch can be recombinant or chimeric, or both. If the gene encodes a desired expression product, activating or deactivating the riboswitch can be used to induce expression of the gene and thus result in production of the expression product. If the gene encodes an inducer or repressor of gene expression or of another cellular process, activation, deactivation or blocking of the riboswitch can result in induction, repression, or de-repression of other, regulated genes or cellular processes. Many such secondary regulatory effects are known and can be adapted for use with riboswitches. An advantage of riboswitches as the primary control for such regulation is that riboswitch trigger molecules can be small, non-antigenic molecules.

Also disclosed are compositions and methods for altering the regulation of a riboswitch by operably linking an aptamer domain to the expression platform domain of the riboswitch (which is a chimeric riboswitch). The aptamer domain can then mediate regulation of the riboswitch through the action of, for example, a trigger molecule for the aptamer domain. Aptamer domains can be operably linked to expression platform domains of riboswitches in any suitable manner, including, for example, by replacing the normal or natural aptamer domain of the riboswitch with the new aptamer domain. Generally, any compound or condition that can activate, deactivate or block the riboswitch from which the aptamer domain is derived can be used to activate, deactivate or block the chimeric riboswitch.

Also disclosed are compositions and methods for inactivating a riboswitch by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule.

Also disclosed are methods of identifying compounds that activate, deactivate or block a riboswitch. For examples, compounds that activate a riboswitch can be identified by bringing into contact a test compound and a riboswitch and assessing activation of the riboswitch. If the riboswitch is activated, the test compound is identified as a compound that activates the riboswitch. Activation of a riboswitch can be assessed in any suitable manner. For example, the riboswitch can be linked to a reporter RNA and expression, expression level, or change in expression level of the reporter RNA can be measured in the presence and absence of the test compound. As another example, the riboswitch can include a conformation dependent label, the signal from which changes depending on the activation state of the riboswitch. Such a riboswitch preferably uses an aptamer domain from or derived from a naturally occurring riboswitch. Assessment of activation of a riboswitch can be performed with the use of a control assay or measurement or without the use of a control assay or measurement. Methods for identifying compounds that deactivate a riboswitch can be performed in analogous ways.

Identification of compounds that block a riboswitch can be accomplished in any suitable manner. For example, an assay can be performed for assessing activation or deactivation of a riboswitch in the presence of a compound known to activate or deactivate the riboswitch and in the presence of a test compound. If activation or deactivation is not observed as would be observed in the absence of the test compound, then the test compound is identified as a compound that blocks activation or deactivation of the riboswitch.

Also disclosed are biosensor riboswitches. Biosensor riboswitches are engineered riboswitches that produce a detectable signal in the presence of their cognate trigger molecule. Useful biosensor riboswitches can be triggered at or above threshold levels of the trigger molecules. Biosensor riboswitches can be designed for use in vivo or in vitro. For example, biosensor riboswitches operably linked to a reporter RNA that encodes a protein that serves as or is involved in producing a signal can be used in vivo by engineering a cell or organism to harbor a nucleic acid construct encoding the riboswitch/reporter RNA. An example of a biosensor riboswitch for use in vitro is a riboswitch that includes a conformation dependent label, the signal from which changes depending on the activation state of the riboswitch. Such a biosensor riboswitch preferably uses an aptamer domain from or derived from a naturally occurring riboswitch. Also disclosed are methods of detecting compounds using biosensor riboswitches. The method can include bringing into contact a test sample and a biosensor riboswitch and assessing the activation of the biosensor riboswitch. Activation of the biosensor riboswitch indicates the presence of the trigger molecule for the biosensor riboswitch in the test sample.

Also disclosed are compounds made by identifying a compound that activates, deactivates or blocks a riboswitch and manufacturing the identified compound. This can be accomplished by, for example, combining compound identification methods as disclosed elsewhere herein with methods for manufacturing the identified compounds. For example, compounds can be made by bringing into contact a test compound and a riboswitch, assessing activation of the riboswitch, and, if the riboswitch is activated by the test compound, manufacturing the test compound that activates the riboswitch as the compound.

Also disclosed are compounds made by checking activation, deactivation or blocking of a riboswitch by a compound and manufacturing the checked compound. This can be accomplished by, for example, combining compound activation, deactivation or blocking assessment methods as disclosed elsewhere herein with methods for manufacturing the checked compounds. For example, compounds can be made by bringing into contact a test compound and a riboswitch, assessing activation of the riboswitch, and, if the riboswitch is activated by the test compound, manufacturing the test compound that activates the riboswitch as the compound. Checking compounds for their ability to activate, deactivate or block a riboswitch refers to both identification of compounds previously unknown to activate, deactivate or block a riboswitch and to assessing the ability of a compound to activate, deactivate or block a riboswitch where the compound was already known to activate, deactivate or block the riboswitch.

Also disclosed are methods for selecting, designing or deriving new riboswitches and/or new aptamers that recognize new trigger molecules. Such methods can involve production of a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results. Also disclosed are riboswitches and aptamer domains produced by these methods.

The disclosed riboswitches, including the derivatives and recombinant forms thereof, generally can be from any source, including naturally occurring riboswitches and riboswitches designed de novo. Any such riboswitches can be used in or with the disclosed methods. However, different types of riboswitches can be defined and some such sub-types can be useful in or with particular methods (generally as described elsewhere herein). Types of riboswitches include, for example, naturally occurring riboswitches, derivatives and modified forms of naturally occurring riboswitches, chimeric riboswitches, and recombinant riboswitches. A naturally occurring riboswitch is a riboswitch having the sequence of a riboswitch as found in nature. Such a naturally occurring riboswitch can be an isolated or recombinant form of the naturally occurring riboswitch as it occurs in nature. That is, the riboswitch has the same primary structure but has been isolated or engineered in a new genetic or nucleic acid context. Chimeric riboswitches can be made up of, for example, part of a riboswitch of any or of a particular class or type of riboswitch and part of a different riboswitch of the same or of any different class or type of riboswitch; part of a riboswitch of any or of a particular class or type of riboswitch and any non-riboswitch sequence or component. Recombinant riboswitches are riboswitches that have been isolated or engineered in a new genetic or nucleic acid context.

Different classes of riboswitches refer to riboswitches that have the same or similar trigger molecules or riboswitches that have the same or similar overall structure (predicted, determined, or a combination). Riboswitches of the same class generally, but need not, have both the same or similar trigger molecules and the same or similar overall structure.

Provided herein is a regulatable gene expression construct comprising a nucleic acid molecule comprising a riboswitch operably linked to a sequence wherein the riboswitch comprises an aptamer domain and an expression platform domain. In certain embodiments, the riboswitch and sequence are heterologous. In certain embodiments, the aptamer domain and the expression platform domain are heterologous. In certain embodiments, the riboswitch and sequence are homologous. In certain embodiments, the aptamer domain and the expression platform domain are heterologous. In certain embodiments, the expression platform domain comprises one or more expression regulatory elements. In certain embodiments, the aptamer domain does not control a ribozyme.

In one aspect, provided herein is a gene expression control device (riboswitch) that includes a chloramphenical resistance gene, linked in 5' to 3' orientation to a theophylline specific aptamer fragment. The 3' end of the theophylline-specific aptamer fragment is linked to a 5' end of the ribosome binding site of the lacI gene followed by the native lacI-lacZ intergenic region containing four lac promoters, two LacI-binding sites and the ribosome binding site of lacZ. When the cassette is inserted into the genome of E. coli MG 1655 upstream from a translational start site of a target gene, the transcription rate of the target gene is controlled by theophylline binding to the aptamer.

In specific embodiments, the theophylline-specific aptamer fragment is operably linked to a linker portion. In certain embodiments, the linker portion is operably linked to a 4, 5, 6, 7, 8 or 9 nucleotide random sequence. In specific embodiments, nucleotide random sequence has 5 nucleotides. In certain embodiments, the target gene is lacZ, rpoS, csrB gene.

In another aspect, provided herein is a target gene transcription control system including a transcriptional repressor protein that represses transcription of the target gene, and two binding sites for the transcriptional repressor protein that are operably linked to the target gene. The system further comprises an ON-riboswitch having an aptamer and an expression platform operably linked to the transcriptional repressor protein of the target gene DNA locus. Binding of a first ligand to the aptamer of the riboswitch induces expression of the transcriptional repressor which in turn decreases expression of the target gene, and binding of a second ligand to the transcriptional repressor protein increases expression of the target gene. In specific embodiments, the first ligand is theophylline. In specific embodiment, the second ligand is IPTG.

In another aspect, provided herein is a target gene control system comprising an ON-lacI riboswitch, a LacI repressor protein, and two LacI binding sites. The ON-lacI riboswitch, the LacI repressor and the LacI-binding sites are positioned on one chromosome. The LacI-binding sites can also be positioned on an extrachromosomal element without affecting the effectiveness of the device in gene regulation.

In another aspect, provided herein is a riboswitch cassette library comprising the following elements in 5' to 3' orientation: a chloramphenical resistance gene, a theophylline-specific aptamer fragment, a linker portion and a 5-nt random sequence. When the cassette is inserted into the genome of *E. coli* MG1655 in a position 5' to the ribosomal binding site of a target gene, transcription of the target gene is controlled by theophylline binding to the aptamer. Transcription of the target gene is detected using standard assay methodology.

In another aspect, provided herewith is a method of detecting DNA clones of an organism. First, a lacI-lacZ construct is formed on the chromosome of the organism. Next, a gene expression control device having a theophylline-specific aptamer fragment is inserted into the genome of the organism at a position upstream to the ribosomal binding site of the lacI-lacZ translational fusion to form a mutant population of organisms. Next, a portion of the DNA mutant population is grown on bromo-chloro-indolyl-galactopyranoside (X-gal) agar plates without theophylline present. Clones from the resultant white colonies of mutant organisms are selected that express no β-galactosidase activity. A portion of the recovered white clones of mutant organisms are grown on X-gal agar plates with theophylline. The resultant blue clones exhibiting β-galactosidase activity are detected using a standard assay.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

In one embodiment, a gene expression control device comprises: a chloramphenical resistance gene, linked in 5' to 3' orientation to a theophylline-specific aptamer fragment; the 3' end of the theophylline-specific aptamer fragment linked to a 5' end of a linker portion and a 5-nt random sequence, in 5' to 3' orientation; a lacI gene preceded by its native ribosome binding site; and a native lacI-lacZ intergenic region containing lac promoters and two LacIbs, wherein when the control device is inserted into the genome of *E. coli* MG1655 upstream from a translational start site of a target gene, a transcription rate of the target gene is controlled by theophylline binding to the aptamer.

In the gene expression control device, the 5-nt random sequence is TGTAT, in a 5' to 3'orientation.

Further, in the gene expression control device, the target gene is selected from the group consisting of a lacZ gene locus, a rpoS gene locus, and a csrB gene locus.

Provided herein is a target gene transcription control system comprises: a transcriptional repressor protein that represses a transcription rate of a DNA locus of the target gene; two binding sites for the transcriptional repressor protein operably linked to the target gene DNA locus; and an ON-riboswitch having an aptamer and an expression platform operably linked to the transcriptional repressor protein of the target gene, wherein binding of a first ligand to the aptamer of the riboswitch decreases expression of the target gene and binding of a second ligand to the transcriptional repressor protein increases transcription of the target gene.

In the target gene transcription control system, binding of the first ligand to the aptamer of the riboswitch induces expression of the transcriptional repressor protein.

Further in the above system, the ON-riboswitch is an ON-lacI riboswitch, the transcriptional repressor protein is a LacI repressor protein, the two binding sites for the transcriptional repressor protein are LacIbs.

Further in the above system, the target gene is selected from the group consisting of a lacZ gene locus, a rpoS gene locus, and a csrB gene locus Further in the above system, the first ligand is theophylline and the second ligand is isopropyl β-D-1-thiogalactopyranoside (IPTG).

Further in the above system, a transcription rate of the target gene is inversely proportional to theophylline concentration within a range of about 100 μM to about 1600 μM, in a bacterial growth medium.

Further in the above system, a transcription rate of the target gene is directly proportional to the isopropyl β-D-1-thiogalactopyranoside (IPTG) concentration within a range of about 0.16 μM to about 40 μM, in a bacterial growth medium.

Also disclosed is an ON-lacI riboswitch having a nucleotide sequence GUAU immediately upstream from the ribosomal binding site wherein the riboswitch forms a stem structure in the absence of theophylline.

Also disclosed is a target gene control system comprising an ON-lacI riboswitch, a lad gene encoding a LacI repressor protein, and two LacIbs binding sites, wherein the ON-lad riboswitch, and the LacI repressor protein are positioned on a chromosome and the LacIbs binding site is positioned on the same chromosome.

Also disclosed is a target gene control system comprising an ON-lacI riboswitch, a lad gene encoding a LacI repressor protein, and two LacIbs binding sites, wherein the ON-lad riboswitch and lacI are positioned on a chromosome and the LacIbs binding site is positioned on an extrachromosomal element.

Also disclosed is a riboswitch cassette library comprising a chloramphenical resistance gene, a theophylline-specific aptamer fragment, a linker portion and a 5-nt random sequence, in 5' to 3' orientation, the lacI gene and two LacIbs (LacI binding sites), wherein when the cassette is inserted into the genome of *E. coli* MG1655 in a position 5' to the ribosome binding site of a target gene, transcription of a target gene is controlled by theophylline binding to the aptamer, and transcription of the target gene is detected using standard assay methodology.

Also disclosed is a method for detecting theophylline sensitive DNA clones of an organism comprising the steps of: a) constructing a lacI-lacZ translational fusion on the chromosome of the organism; b) inserting a gene expression control device comprising a theophylline-specific aptamer fragment into the genome of the organism at a position 5' to the ribosomal binding site of the lacI-lacZ translational fusion to form a DNA mutant population; c) growing a portion of the DNA mutant population of step b on X-gal agar plates without theophylline; d) selecting clones from resultant white colonies of DNA mutant organisms expressing no β-galactosidase activity, as determined by a standard assay; e) growing a portion of the resultant white clones of DNA mutant organisms from step d on X-gal agar plates with theophylline; and f) detecting blue clones exhibiting β-galactosidase activity by using a standard assay.

4. BRIEF DESCRIPTION OF THE DRAWINGS

FIG. 4A is a schematic drawing showing the predicted structure of the ON1-lacI riboswitch in the presence and absence of theophylline, in accordance with one embodiment. FIG. 4A discloses SEQ ID NOS 7, 8, 7 and 9, respectively, in order of appearance FIG. 4B is a schematic drawing showing the predicted structure of the ON2-lacI riboswitch in the presence and absence of theophylline, in accordance with one embodiment. FIG. 4B discloses SEQ ID NOS 7, 10 and 11, respectively, in order of appearance.

FIG. 5A is a schematic drawing showing the predicted structure of an OFF-lacI riboswitch in the presence and absence of theophylline, in accordance with one embodiment. FIG. 5A discloses SEQ ID NOS 7, 12, 7 and 13, respectively, in order of appearance.

FIG. 5B is a schematic drawing showing the structure of a mutant stem (10 nt) loop structure immediately upstream of the RBS of lacI fused with lacZ in accordance with one embodiment. FIG. 5B discloses SEQ ID NOS 7 and 14, respectively, in order of appearance.

Figure 6:
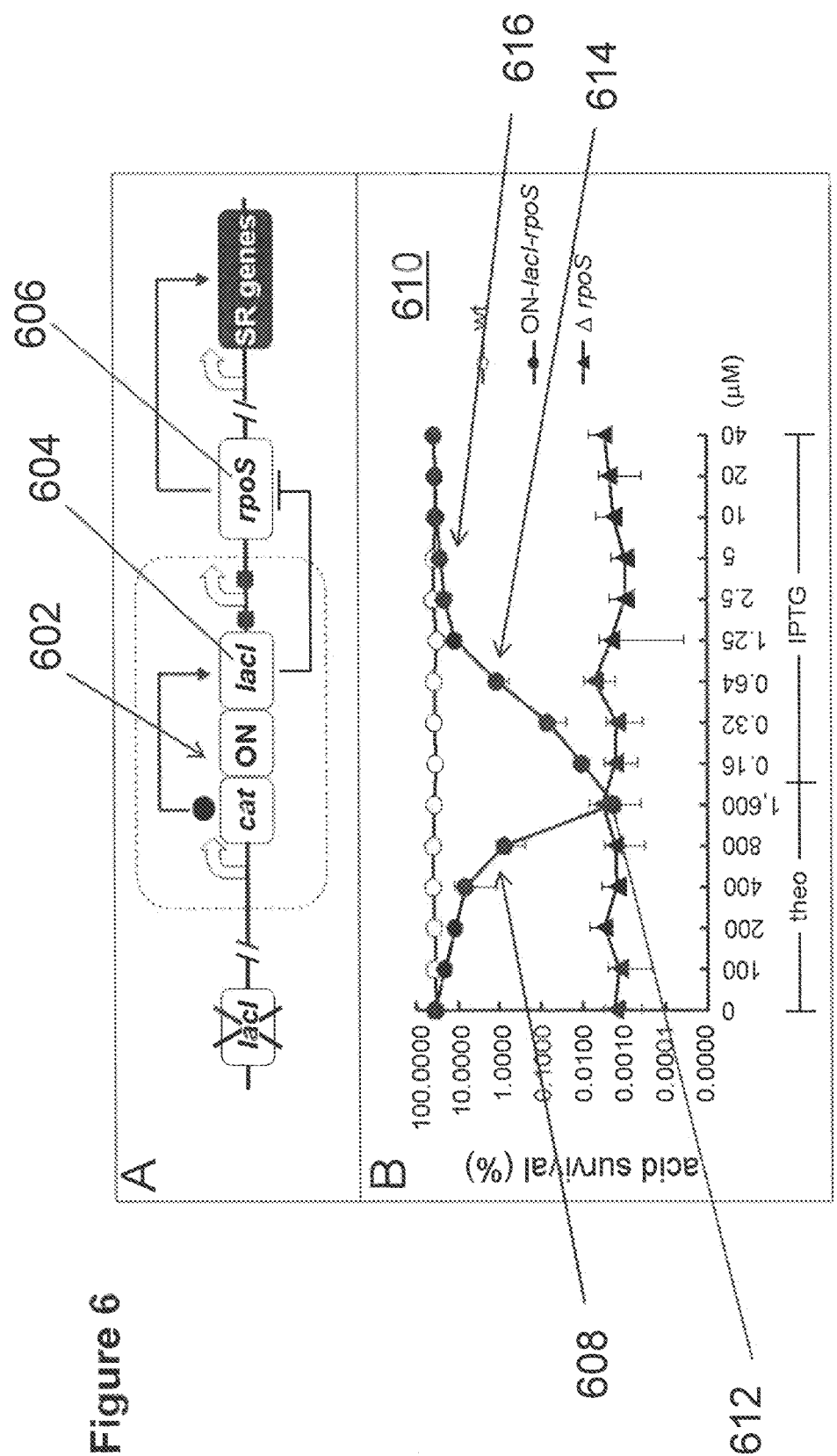

FIG. 6A is a schematic illustration of a portable riboswitch system, in accordance with one embodiment.

FIG. 6B is a graph showing portable, tunable, two-way control of the rpoS gene, in accordance with one embodiment.

Figure 7:
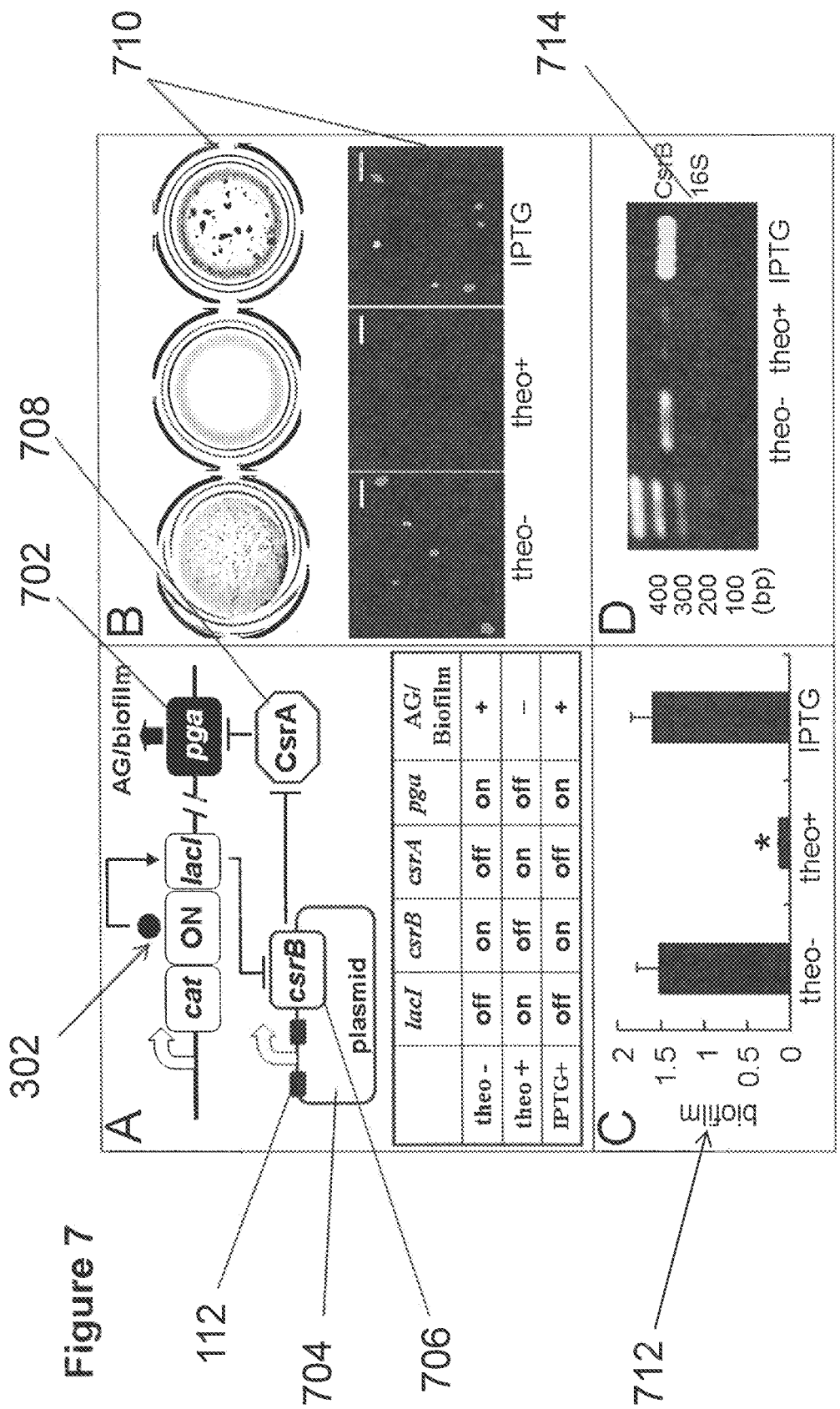

FIG. 7A is a schematic representation of a trans-acting gene control system and the corresponding phenotypic changes in autoaggregation and biofilm formation of an *E. coli* strain carrying pLacIb-CsrB and an ON-lacI riboswitch, in accordance with one embodiment.

FIG. 7B presents scanned images and fluorescent microscopic images of cell suspensions of an ON-lacI *E. coli* strain that harbors a pLacIb-CsrB construct, in accordance with one embodiment.

FIG. 7C is a graph of the effects of theophylline and IPTG on biofilm formation by an ON-lacI *E. coli* strain that harbors a pLacIb-CsrB construct, in accordance with one embodiment.

FIG. 7D is an agarose gel image showing levels of intracellular CsrB, small, noncoding RNA isolated from an ON-lacI *E. coli* strain that harbors a pLacIb-CsrB construct after PCR amplification, in accordance with one embodiment.

Figure 8:
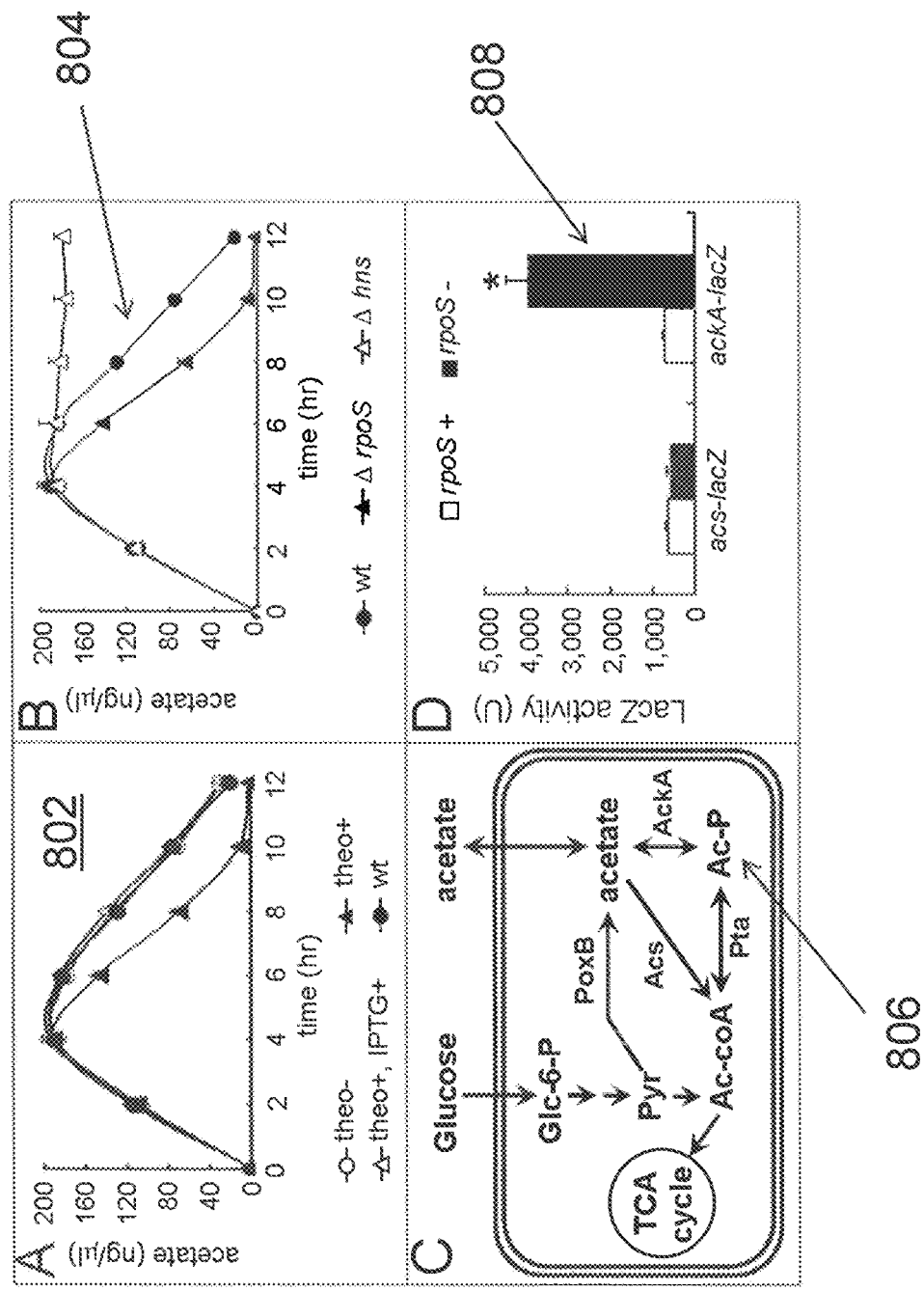

FIG. 8A is a graph showing extracellular acetate concentrations plotted as a function of time for wild type and ON-lacI-rpoS strain *E. coli*, in accordance with one embodiment.

FIG. 8B is a graph showing extracellular acetate concentrations as a function of time for wild type *E. coli*, rpoS deficient *E. coli*, and has deficient *E. coli*, in accordance with one embodiment.

FIG. 8C is a schematic diagram showing the pathways of acetate assimilation in *E. coli*.

FIG. 8D is a graph showing lacZ activities of strains of *E. coli* carrying the acs-lacZ or ackA-lacZ translational fusion, with or without rpoS, in accordance with one embodiment.

5. DETAILED DESCRIPTION

Provided herein is a portable regulatable gene expression construct comprising a two-way riboswitch operably linked to a target gene. The riboswitch comprises an aptamer domain, expression platform domain, repressor protein and its binding sites.

The aptamer domain of the riboswitch conforms to a highly conserved consensus sequence and structure. Thus, sequence homology searches can be used to identify related riboswitch aptamer domains. Described herein is a method using a riboswitch cassette library comprising a stretch of random sequence operably linked to the aptamer and repressor protein, and its binding sites. In certain embodiments, the aptamer domains for riboswitch RNAs are about 70 to 170 nucleotides in length. In certain embodiments, the aptamer domain of the riboswitch as provided herein is a natural aptamer sequence. In certain embodiments, the aptamer domains are artificial aptamers that function with high affinity and selectivity. The affinity and selectivity of artificial aptamers for the target ligand can be assayed by routine methods as known in the art. In certain embodiments, the construct comprises a termination signal for the termination of transcription.

In certain embodiments, provided herein are variant riboswitches that respond to theophylline. These riboswitches carry an aptamer domain that corresponds closely in sequence and secondary structure to the theophylline-specific aptamer. The variant riboswitches carries 1, 2, 3, 4, 5 or 6 mutations in the conserved core of the aptamer. In certain embodiments, the variant riboswitches carries 1-5, 6-10, 11-15, 16-20 mutations in the aptamer. In one embodiment, the theophylline-specific aptamer comprises a nucleotide sequence of ATACCAGCATCGTCTTGATGC-CCTTGGCAG (SEQ ID NO: 1) (AUACCAGCAUCGUCU-UGAUGCCCUUGGCAG—FIGS. 4A, 4B, and 5A) (SEQ ID NO: 2).

Disclosed are isolated and recombinant riboswitches, recombinant constructs containing such riboswitches, heterologous sequences operably linked to such riboswitches, and cells and transgenic organisms harboring such riboswitches, riboswitch recombinant constructs, and riboswitches operably linked to heterologous sequences. The heterologous sequences can be, for example, sequences encoding proteins or peptides of interest, including reporter proteins or peptides. Preferred riboswitches are, or are derived from, naturally occurring riboswitches.

The disclosed riboswitches, including the derivatives and recombinant forms thereof, generally can be from any source, including naturally occurring riboswitches and riboswitches designed de novo. Any such riboswitches can be used in or with the disclosed methods. However, different types of riboswitches can be defined and some such sub-types can be useful in or with particular methods. Types of riboswitches include, for example, naturally occurring riboswitches, derivatives and modified forms of naturally occurring riboswitches, chimeric riboswitches, and recombinant riboswitches. A naturally occurring riboswitch is a riboswitch having the sequence of a riboswitch as found in nature. Such a naturally occurring riboswitch can be an isolated or recombinant form of the naturally occurring riboswitch as it occurs in nature. That is, the riboswitch has the same primary structure but is different from the riboswitch that occurs in nature. Recombinant riboswitches are riboswitches that have been isolated or engineered using recombinant technology.

Also disclosed are chimeric riboswitches containing heterologous aptamer domains and expression platform domains That is, chimeric riboswitches are made up an aptamer domain from one source and an expression platform domain from another source. The heterologous sources can be from, for example, different specific riboswitches, different types of riboswitches, or different classes of riboswitches. The heterologous aptamers can also come from non-riboswitch aptamers. The heterologous expression platform domains can also come from non-riboswitch sources.

Riboswitches can be modified from other known, developed or naturally-occurring riboswitches. For example, switch domain portions can be modified by changing one or more nucleotides while preserving the known or predicted secondary, tertiary, or both secondary and tertiary structure of the riboswitch. For example, both nucleotides in a base pair can be changed to nucleotides that can also base pair. Changes that allow retention of base pairing are referred to herein as base pair conservative changes.

Modified or derivative riboswitches can also be produced using in vitro selection and evolution techniques. In general, in vitro evolution techniques as applied to riboswitches involve producing a set of variant riboswitches where part(s) of the riboswitch sequence is varied while other parts of the riboswitch are held constant. Activation, deactivation or blocking (or other functional or structural criteria) of the set of variant riboswitches can then be assessed and those variant riboswitches meeting the criteria of interest are selected for use or further rounds of evolution.

Also disclosed are modified riboswitches with altered regulation. The regulation of a riboswitch can be altered by operably linking an aptamer domain to the expression platform domain of the riboswitch (which is a chimeric riboswitch). The aptamer domain can then mediate regulation of the riboswitch through the action of, for example, a trigger molecule for the aptamer domain. Aptamer domains can be operably linked to expression platform domains of riboswitches in any suitable manner, including, for example, by replacing the normal or natural aptamer domain of the riboswitch with the new aptamer domain. Generally, any compound or condition that can activate, deactivate or block the riboswitch from which the aptamer domain is derived can be used to activate, deactivate or block the chimeric riboswitch.

Also disclosed are inactivated riboswitches. Riboswitches can be inactivated by covalently altering the riboswitch (by, for example, crosslinking parts of the riboswitch or coupling a compound to the riboswitch). Inactivation of a riboswitch in this manner can result from, for example, an alteration that prevents the trigger molecule for the riboswitch from binding, that prevents the change in state of the riboswitch upon binding of the trigger molecule, or that prevents the expression platform domain of the riboswitch from affecting expression upon binding of the trigger molecule.

Also disclosed are modified or derivative riboswitches that recognize new trigger molecules. New riboswitches and/or new aptamers that recognize new trigger molecules can be selected for, designed or derived from known riboswitches. This can be accomplished by, for example, producing a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results.

Particularly useful aptamer domains can form a stem structure referred to herein as the P1 stem structure (or simply P1). The hybridizing strands in the P1 stem structure are referred to as the aptamer strand (also referred to as the P1a strand) and the control strand (also referred to as the P1b strand). The control strand can form a stem structure with both the aptamer strand and a sequence in a linked expression platform that is referred to as the regulated strand (also referred to as the P1c strand). Thus, the control strand (P1b) can form alternative stem structures with the aptamer strand (P1a) and the regulated strand (P1c). Activation or deactivation of a riboswitch results in a shift from one of the stem structures to the other (from P1a/P1b to P1b/P1c or vice versa). The formation of the P1b/P1c stem structure affects expression of the RNA molecule containing the riboswitch. Riboswitches that operate via this control mechanism are referred to herein as alternative stem structure riboswitches (or as alternative stem riboswitches).

In general, any aptamer domain can be adapted for use with any expression platform domain by designing or adapting a regulated strand in the expression platform domain to be complementary to the control strand of the aptamer domain. Alternatively, the sequence of the aptamer and control strands of an aptamer domain can be adapted so that the control strand is complementary to a functionally significant sequence in an expression platform.

In certain embodiments, the speed of transcription and spacing of the riboswitch and expression platform elements are increased or decreased for proper control. Transcription speed can be adjusted by, for example, by including polymerase pausing elements (e.g., a series of uridine residues) to pause transcription and allow the riboswitch to form and sense trigger molecules.

Disclosed are regulatable gene expression constructs comprising a nucleic acid molecule encoding an RNA comprising a riboswitch operably linked to a coding region, wherein the riboswitch regulates expression of the RNA, wherein the riboswitch and coding region are heterologous. The riboswitch can comprise an aptamer domain and an expression platform domain, wherein the aptamer domain and the expression platform domain are heterologous. The riboswitch can comprise an aptamer domain and an expression platform domain, wherein the aptamer domain comprises a P1 stem, wherein the P1 stem comprises an aptamer strand and a control strand, wherein the expression platform domain comprises a regulated strand, wherein the regulated strand, the control strand, or both have been designed to form a stem structure.

Disclosed are riboswitches, wherein the riboswitch is a non-natural derivative of a naturally-occurring riboswitch. The riboswitch can comprise an aptamer domain and an expression platform domain, wherein the aptamer domain and the expression platform domain are heterologous. The riboswitch can be derived from a naturally-occurring theophylline-responsive riboswitch. The riboswitch can be activated by a trigger molecule, wherein the riboswitch produces a signal when activated by the trigger molecule.

Numerous riboswitches and riboswitch constructs are described and referred to herein. It is specifically contemplated that any specific riboswitch or riboswitch construct or group of riboswitches or riboswitch constructs can be excluded from some aspects of the invention disclosed herein.

Provided herein are aptamer domains of riboswitches, which can be derived from any source, including, for example, natural aptamer domains of riboswitches, artificial aptamers, engineered, selected, evolved or derived aptamers or aptamer domains. Aptamers in riboswitches generally have at least one portion that can interact, such as by forming a stem structure, with a portion of the linked expression platform domain. This stem structure will either form or be disrupted upon binding of the trigger molecule.

In certain embodiments, naturally occurring aptamer domains can be modified to produce modified or variant aptamer domains that are useful in the riboswitch. Conservative modifications include any change in base paired nucleotides such that the nucleotides in the pair remain complementary.

In certain embodiments, the P1 stem and its constituent strands can be modified in adapting aptamer domains for use with expression platforms and RNA molecules. Such modifications, which can be extensive, are referred to herein as P1 modifications. P1 modifications include changes to the sequence and/or length of the P1 stem of an aptamer domain.

In certain embodiments, aptamer domains of the disclosed riboswitches can also be used for any other purpose, and in any other context, as aptamers. For example, aptamers can be used to control ribozymes, other molecular switches, and any RNA molecule where a change in structure can affect function of the RNA.

Expression platform domains are a part of riboswitches that affect expression of the RNA molecule that contains the riboswitch. Expression platform domains generally have at least one portion that can interact, such as by forming a stem structure, with a portion of the linked aptamer domain. This stem structure will either form or be disrupted upon binding of the trigger molecule. The stem structure generally either is, or prevents formation of, an expression regulatory structure. An expression regulatory structure is a structure that allows, prevents, enhances or inhibits expression of an RNA molecule containing the structure. Examples include initiation codons, transcription terminators, and stability and processing signals.

Trigger molecules are molecules and compounds that can activate a riboswitch. This includes the natural or normal trigger molecule for the riboswitch and other compounds that can activate the riboswitch. Natural or normal trigger molecules are the trigger molecule for a given riboswitch in nature or, in the case of some non-natural riboswitches, the trigger molecule for which the riboswitch was designed or with which the riboswitch was selected (as in, for example, in vitro selection or in vitro evolution techniques). Non-natural trigger molecules can be referred to as non-natural trigger molecules.

Also disclosed are compounds, and compositions containing such compounds, that can activate, deactivate or block a riboswitch. In certain embodiments, the compounds are ligands. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. A riboswitch can be blocked by, for example, binding of an analog of the trigger molecule that does not activate the riboswitch.

Also disclosed are compounds for altering expression of an RNA molecule, or of a gene encoding an RNA molecule, where the RNA molecule includes a riboswitch. This can be accomplished by bringing a compound into contact with the RNA molecule.

Riboswitches function to control gene expression through the binding or removal of a trigger molecule. Thus, subjecting an RNA molecule of interest that includes a riboswitch to conditions that activate, deactivate or block the riboswitch can be used to alter expression of the RNA. Expression can be altered as a result of, for example, termination of transcription or blocking of ribosome binding to the RNA. Binding of a trigger molecule can, depending on the nature of the riboswitch, reduce or prevent expression of the RNA molecule or promote or increase expression of the RNA molecule.

Also disclosed are methods of identifying compounds that activate, deactivate or block a riboswitch. For examples, compounds that activate a riboswitch can be identified by bringing into contact a test compound and a riboswitch and assessing activation of the riboswitch. If the riboswitch is activated, the test compound is identified as a compound that activates the riboswitch. Activation of a riboswitch can be assessed in any suitable manner. For example, the riboswitch can be linked to a reporter RNA and expression, expression level, or change in expression level of the reporter RNA can be measured in the presence and absence of the test compound. As another example, the riboswitch can include a conformation dependent label, the signal from which changes depending on the activation state of the riboswitch. Such a riboswitch preferably uses an aptamer domain from or derived from a naturally occurring riboswitch. As can be seen, assessment of activation of a riboswitch can be performed with the use of a control assay or measurement or without the use of a control assay or measurement. Methods for identifying compounds that deactivate a riboswitch can be performed in analogous ways.

Identification of compounds that block a riboswitch can be accomplished in any suitable manner. For example, an assay can be performed for assessing activation or deactivation of a riboswitch in the presence of a compound known to activate or deactivate the riboswitch and in the presence of a test compound. If activation or deactivation is not observed as would be observed in the absence of the test compound, then the test compound is identified as a compound that blocks activation or deactivation of the riboswitch.

The disclosed riboswitches can be used in with any suitable expression system. Recombinant expression is usefully accomplished using a vector, such as a plasmid. The vector can include a promoter operably linked to riboswitch-encoding sequence and RNA to be expression (e.g., RNA encoding a protein). The vector can also include other elements required for transcription and translation. Vectors include but are not limited to plasmids, viral nucleic acids, viruses, phage nucleic acids, phages, cosmids, and artificial chromosomes. A variety of prokaryotic and eukaryotic expression vectors suitable for carrying riboswitch-regulated constructs can be produced. Such expression vectors include, for example, pET, pET3d, pCR2.1, pBAD, pUC, and yeast vectors. The vectors can be used, for example, in a variety of in vivo and in vitro situation.

Viral vectors include adenovirus, adeno-associated virus, herpes virus, vaccinia virus, polio virus, AIDS virus, neuronal trophic virus, Sindbis and other RNA viruses, including these viruses with the HIV backbone. Also useful are any viral families which share the properties of these viruses which make them suitable for use as vectors. Retroviral vectors, which are described in Verma (1985), include Murine Maloney Leukemia virus, MMLV, and retroviruses that express the desirable properties of MMLV as a vector. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA.

In certain embodiments, the construct comprises a promoter. A "promoter" is generally a sequence or sequences of DNA that function when in a relatively fixed location in regard to the transcription start site. A "promoter" contains core elements required for basic interaction of RNA polymerase and transcription factors and can contain upstream elements and response elements.

In certain embodiments, the construct comprises an enhancer. "Enhancer" generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the constructs.

The vector can include nucleic acid sequence encoding a marker product. This marker product is used to determine if the gene has been delivered to the cell and once delivered is being expressed. Preferred marker genes are the *E. coli* lacZ gene which encodes beta-galactosidase and the gfp gene which encodes green fluorescent protein.

In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs chloramphenical, neomycin, (Southern and Berg, 1982), mycophenolic acid, (Mulligan and Berg, 1980) or hygromycin (Sugden et al., 1985).

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991).

For assessing activation of a riboswitch, a reporter protein or peptide can be used. The reporter protein or peptide can be encoded by the RNA the expression of which is regulated by the riboswitch. The examples describe the use of some specific reporter proteins. The use of reporter proteins and peptides is well known and can be adapted easily for use with riboswitches. The reporter proteins can be any protein or peptide that can be detected or that produces a detectable signal. Preferably, the presence of the protein or peptide can be detected using standard techniques (e.g., radioimmunoassay, radio-labeling, immunoassay, assay for enzymatic activity, absorbance, fluorescence, luminescence, and Western blot). More preferably, the level of the reporter protein is easily quantifiable using standard techniques even at low levels. Useful reporter proteins include luciferases, green fluorescent proteins and their derivatives, such as firefly luciferase (FL) from *Photinus pyralis*, and *Renilla* luciferase (RL) from *Renilla reniformis*.

In general, it is understood that one way to define any known variants and derivatives or those that might arise, of the disclosed riboswitches, aptamers, expression platforms, genes and proteins herein, is through defining the variants and derivatives in terms of homology to specific known sequences. In general, variants of riboswitches, aptamers, expression platforms, genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to a stated sequence or a native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman, *Adv. Appl. Math.* 2:482 (1981), by the homology alignment algorithm of Needleman and Wunsch, *J Mol. Biol.* 48:443 (1970), by the search for similarity method of Pearson and Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science*, 244:48-52, 1989, Jaeger et al. *Proc. Natl. Acad. Sci. USA* 86:7706-7710, 1989, Jaeger et al., *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

The term hybridization typically means a sequence driven interaction between at least two nucleic acid molecules, such as a primer or a probe and a riboswitch or a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

There are a variety of molecules disclosed herein that are nucleic acid based, including, for example, riboswitches, aptamers, and nucleic acids that encode riboswitches and aptamers. The disclosed nucleic acids can be made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if a nucleic acid molecule is introduced into a cell or cell environment through for example exogenous delivery, it is advantageous that the nucleic acid molecule be made up of nucleotide analogs that reduce the degradation of the nucleic acid molecule in the cellular environment.

So long as their relevant function is maintained, riboswitches, aptamers, expression platforms and any other oligonucleotides and nucleic acids can be made up of or include modified nucleotides (nucleotide analogs). Many modified nucleotides are known and can be used in oligonucleotides and nucleic acids. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and 0-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as T-O-methoxyethyl, to achieve unique properties such as increased duplex stability. There are numerous U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Solid supports are solid-state substrates or supports with which molecules (such as trigger molecules) and riboswitches (or other components used in, or produced by, the disclosed methods) can be associated. Riboswitches and other molecules can be associated with solid supports directly or indirectly. For example, analytes (e.g., trigger molecules, test compounds) can be bound to the surface of a solid support or associated with capture agents (e.g., compounds or molecules that bind an analyte) immobilized on solid supports. As another example, riboswitches can be bound to the surface of a solid support or associated with probes immobilized on solid supports. An array is a solid support to which multiple riboswitches, probes or other molecules have been associated in an array, grid, or other organized pattern.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

An array can include a plurality of riboswitches, trigger molecules, other molecules, compounds or probes immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification.

Although useful, it is not required that the solid support be a single unit or structure. A set of riboswitches, trigger molecules, other molecules, compounds and/or probes can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci. USA* 91(11):5022-5026 (1994), and Khrapko et al., *Mol Biol* (Mosk) (USSR) 25:718-730 (1991). A method for immobilization of 3'-amine oligonucleotides on casein-coated slides is described by Stimpson et al., *Proc. Natl. Acad. Sci.* USA 92:6379-6383 (1995). A useful method of attaching oligonucleotides to solid-state substrates is described by Guo et al., *Nucleic Acids Res.* 22:5456-5465 (1994).

Each of the components (for example, riboswitches, trigger molecules, or other molecules) immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting compounds, the kit comprising one or more biosensor riboswitches. The kits also can contain reagents and labels for detecting activation of the riboswitches.

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising iosensor riboswitches, a solid support and a signal-reading device.

Disclosed are data structures used in, generated by, or generated from, the disclosed method. Data structures generally are any form of data, information, and/or objects collected, organized, stored, and/or embodied in a composition or medium. Riboswitch structures and activation measurements stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

Disclosed are methods for activating, deactivating or blocking a riboswitch. Such methods can involve, for example, bringing into contact a riboswitch and a compound or trigger molecule that can activate, deactivate or block the riboswitch. Riboswitches function to control gene expression through the binding or removal of a trigger molecule. Compounds can be used to activate, deactivate or block a riboswitch. The trigger molecule for a riboswitch (as well as other activating compounds) can be used to activate a riboswitch. Compounds other than the trigger molecule generally can be used to deactivate or block a riboswitch. Riboswitches can also be deactivated by, for example, removing trigger molecules from the presence of the riboswitch. Thus, the disclosed method of deactivating a riboswitch can involve, for example, removing a trigger molecule (or other activating compound) from the presence or contact with the riboswitch. A riboswitch can be blocked by, for example, binding of an analog of the trigger molecule that does not activate the riboswitch.

Also disclosed are methods for selecting, designing or deriving new riboswitches and/or new aptamers that recognize new trigger molecules. Such methods can involve production of a set of aptamer variants in a riboswitch, assessing the activation of the variant riboswitches in the presence of a compound of interest, selecting variant riboswitches that were activated (or, for example, the riboswitches that were the most highly or the most selectively activated), and repeating these steps until a variant riboswitch of a desired activity, specificity, combination of activity and specificity, or other combination of properties results. Also disclosed are riboswitches and aptamer domains produced by these methods.

Techniques for in vitro selection and in vitro evolution of functional nucleic acid molecules are known and can be adapted for use with riboswitches and their components. Useful techniques are described by, for example, A. Roth and R. R. Breaker (2003) Selection in vitro of allosteric ribozymes. In: Methods in Molecular Biology Series—Catalytic Nucleic Acid Protocols (Sioud, M., ed.), Humana, Totowa, N.J.; R. R. Breaker (2002) Engineered Allosteric Ribozymes as Biosensor Components. Curr. Opin. Biotechnol. 13:31-39; G. M. Emilsson and R. R. Breaker (2002) Deoxyribozymes: New Activities and New Applications. *Cell. Mol. Life Sci.* 59:596-607; Y. Li, R. R. Breaker (2001) In vitro Selection of Kinase and Ligase Deoxyribozymes. Methods 23:179-190; G. A. Soukup, R. R. Breaker (2000) Allosteric Ribozymes. In: Ribozymes: Biology and Biotechnology. R. K. Gaur and G. Krupp eds. Eaton Publishing; G. A. Soukup, R. R. Breaker (2000) Allosteric Nucleic Acid Catalysts. Curr. Opin. Struct. Biol. 10:318-325; G. A. Soukup, R. R. Breaker (1999) Nucleic Acid Molecular Switches. *Trends Biotechnol.* 17:469-476; R. R. Breaker (1999) In vitro Selection of Self-cleaving Ribozymes and Deoxyribozymes. In: Intracellular Ribozyme Applications: Principles and Protocols. L. Couture, J Rossi eds. *Horizon Scientific Press,* Norfolk, England; R. R. Breaker (1997) In vitro Selection of Catalytic Polynucleotides. *Chem. Rev.* 97:371-390; and references cited therein; each of these publications being specifically incorporated herein by reference for their description of in vitro selections and evolution techniques.

Throughout this specification, like numbers refer to like elements.

Provided herein is a target-specific riboswitch device, and a method for constructing and detecting such devices. In one embodiment, a riboswitch device is constructed that achieves two-way control of gene expression in microorganisms, enabling the target genes to be reversibly regulated without changing the growth environment of the micro-organisms. In certain embodiments, the device is a regulatable gene expression construct.

In one embodiment, off-on riboswitches are constructed that have a theophylline responsive aptamer as the sensor domain. These riboswitches adopt multiple conformations at equilibrium within the chromosome of the host micro-organism. Some of the conformations permit downstream target gene expression; others repress target gene expression. If theophylline binding to the aptamer favors the formation of conformations that permit target expression, then the riboswitch is an ON-switch. Conversely, if theophylline binding shifts the equilibrium distribution to conformations that repress target expression, the riboswitch is an OFF-switch.

In one embodiment, a riboswitch library is constructed and used to screen for clones that effectively control the expression of a target gene in response to theophylline. First, DNA is isolated from an E. coli ON-switch-csrA mutant having a theophylline responsive ON-riboswitch for the csrA gene. The theophylline-specific aptamer fragment is amplified using polymerase chain reaction (PCR) methodology. Next the aptamer is linked to a chloramphenical resistance gene (cat) using PCR ligation methodology, generating a riboswitch cassette library containing a cat-aptamer-linker-random fragment sequence on the chromosome. The cat gene facilitates recombinant engineering (recombineering) techniques to insert the cassette into the genome, and the 5 nt-random sequence allows construction of a riboswitch library. Using recombineering methods, the cassette is integrated into the genome of the *E. coli* MG1655 strain immediately upstream of the ribosome binding site (RBS) for the target genes, resulting in numerous mutant strains. Each of the mutant strains carries a riboswitch candidate (functional or nonfunctional) on the chromosome. In theory, the mutant library contains $4^5$ (1024) riboswitch candidates.

In one embodiment, the *E. coli* crp gene is selected for control using a riboswitch. The crp gene encodes the cyclic AMP receptor protein (CRP), a global regulator that controls transcription initiation of over 180 genes, including the lacZ gene. The CRP protein is a positive regulator of the lacZ gene, which produces β-galactosidase enzyme. Therefore, the CRP protein concentration is linearly correlated with β-galactosidase levels, allowing crp gene expression to be detected by examining the levels of β-galactosidase production. When the *E. coli* is maintained on plates containing bromo-chloro-indolyl-galactopyranoside (X-gal) as an indicator, crp gene expression in an *E. coli* colony can be detected by a blue color. Alternatively, β-galactosidase can be quantified using a standard β-galactosidase assay.

Described herein are examples illustrating various embodiments provided herein.

Example 1

*E. coli* strain MG1655 was used. All bacterial strains were grown at 37° C., with shaking at 220 rpm, in Luria-Bertani (LB) medium. The antibiotics ampicillin (50 μg/ml), kanamycin (50 μg/ml), and chloramphenicol (12.5 μg/ml) were used for selection when appropriate.

Figure 1:
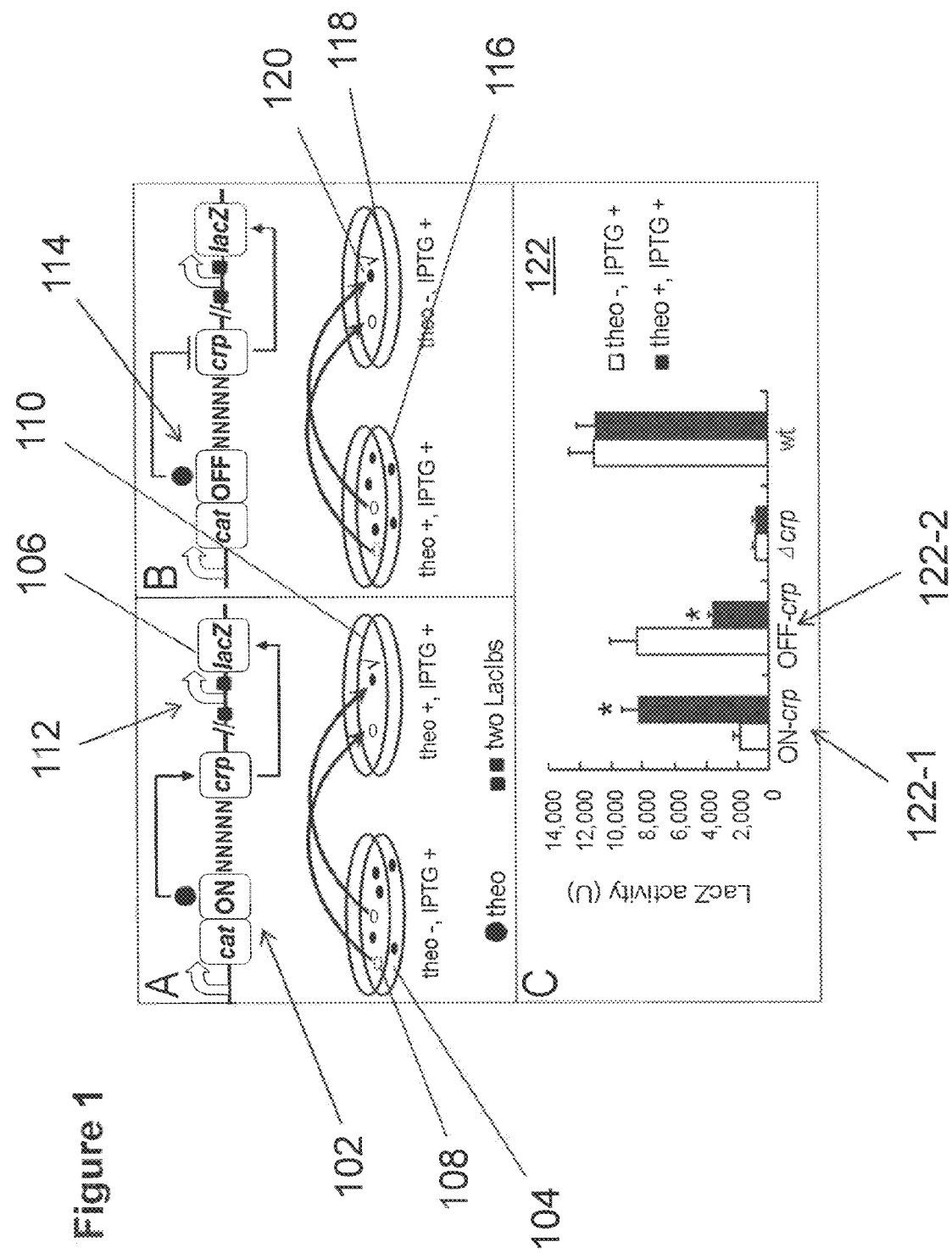
FIG. 1A is a schematic illustration of the construction of an ON riboswitch for the cyclic AMP receptor protein (encoded by "crp"). The crp gene detected by using a library screening-based method, in accordance with one embodiment.
FIG. 1B is a schematic illustration of the construction of an OFF riboswitch for the crp gene detected by using a library screening-based method, in accordance with one embodiment.
FIG. 1C is a graph showing the lacZ activities of the ON-crp, OFF-crp, Δcrp mutants and wild type *E. coli* MG1655 in the presence and absence of 2 mM theophylline, in accordance with one embodiment.

To screen for operational ON-riboswitches for the crp gene, the mutant strain of *E. coli* MG1655 containing riboswitch cassette 102 (cat-aptamer-linker-random sequence) was grown on agar plates 104 with 0.06 mg/ml X-gal and 1 mM IPTG but without theophylline (FIG. 1A). Because CRP is required for lacZ 106 transcription, low levels of CRP will result in white colonies 108. Therefore, white colonies 108 grown on X-gal agar plates 104 without theophylline were selected. Approximately 1500 colonies were screened for color. Five colonies appeared white relative to the others. These 5 colonies were placed on agar plates 110 with 1 mM IPTG and 2 mM theophylline. After culturing for 24 hours, 3 clones formed blue colonies, indicating that they carried ON riboswitches that turned on the crp gene, enabling lacZ expression (as revealed by blue color) in response to theophylline. The darkest blue clone (ON-crp strain) on the agar plates 110 including theophylline was chosen for further testing. Its responsiveness to theophylline was verified using a standard β-galactosidase assay; the results of the assay are shown in graph 122, column 122-1, in FIG. 1C. Sequencing results reveal that the 5 nt-random sequence in ON-crp is CATGC (CAUGC).

Figure 2:
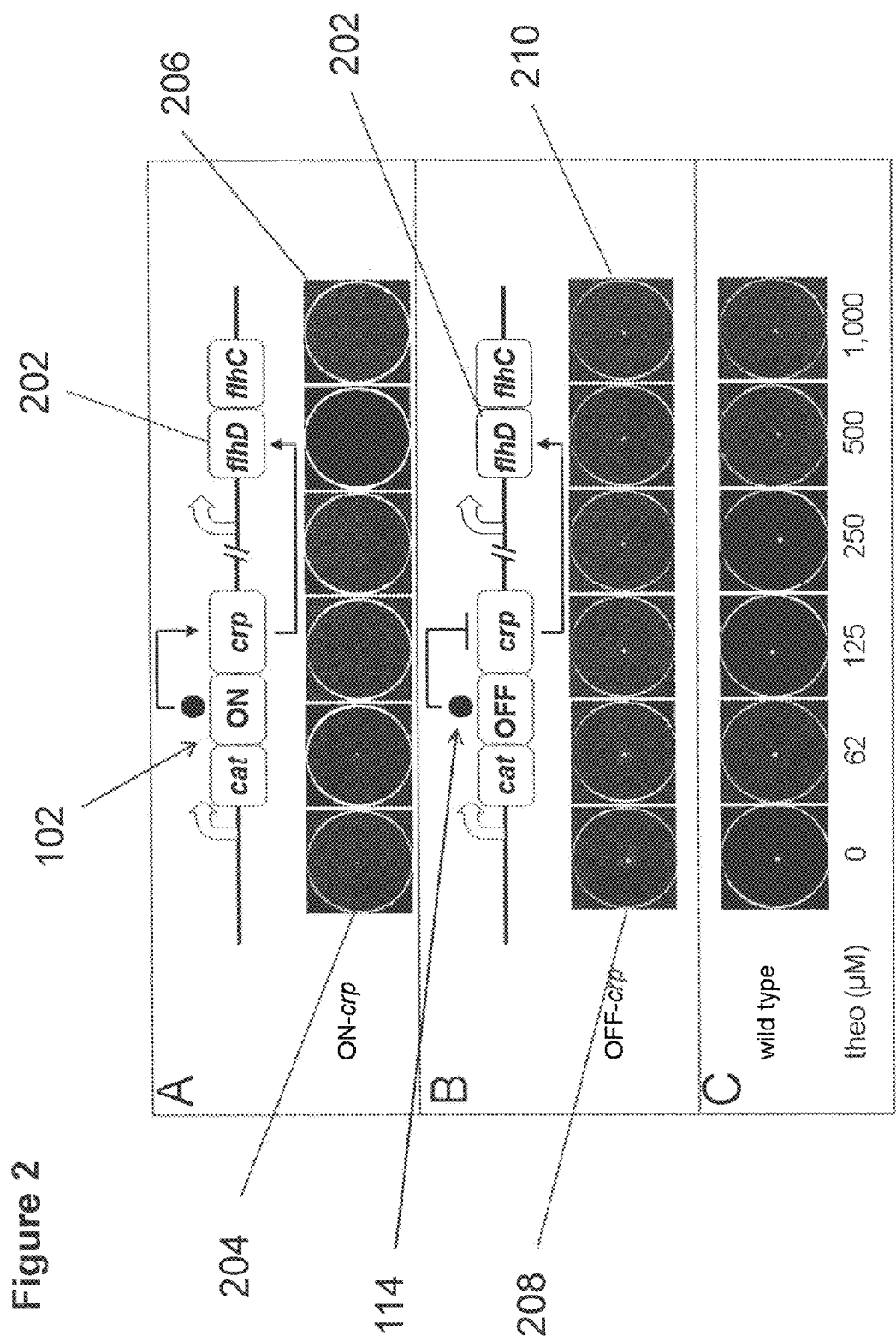
FIG. 2A is an illustration of motility of the ON-crp strain of *E. coli* MG1655 in the presence of increasing concentrations of theophylline, in accordance with one embodiment.
FIG. 2B is an illustration of motility of the OFF-crp strain of *E. coli* MG1655 in the presence of increasing concentrations of theophylline, in accordance with one embodiment.
FIG. 2C is an illustration of motility of the wild-type strain of *E. coli* MG1655 in the presence of increasing concentrations of theophylline.

CRP has previously been demonstrated to enhance bacterial motility by activating the transcription of the ADC master operon 202, shown in FIG. 2A. The motility phenotype of the ON-crp strain was assayed to further confirm the effectiveness of the ON-riboswitch. The ON-crp strain showed poor motility on semisolid motility plates 204 in the absence of theophylline, but gained motility when the theophylline ligand was added, as shown in plate 206 (FIG. 2A). In addition, the motility of the ON-crp strain increased with higher theophylline concentrations, indicating that theophylline initiates translation of the crp gene in a concentration-dependent manner, and therefore, the ON-riboswitch can be used to fine-tune the crp gene expression.

Example 2

To screen for operational OFF switches 114 for the crp gene (FIG. 1B) the mutant strain of *E. coli* MG1655 containing cassette 102 (described above) was first plated on X-gal plates 116 with both 1 mM IPTG and 2 mM theophylline. White colonies were selected based on the assumption that they possibly carried OFF-riboswitches and turned off crp gene expression in response to theophylline. Approximately 3000 colonies were screened, and 5 appeared white compared to the other colonies. The white colonies were cultured on X-gal plates 118 with 1 mM IPTG but without theophylline. One blue clone was obtained, indicating that this clone had little crp expression in the presence of theophylline but considerable crp expression in the absence of the theophylline ligand. Thus, this clone (OFF-crp) carried a theophylline sensitive OFF-riboswitch for the crp gene. Sequencing results showed that its random sequence is CCGGA. A β-galactosidase assay confirmed the effectiveness of OFF-crp in regulating crp expression; (FIG. 1C, graph 122, column 122-2). Furthermore, OFF-crp finely tuned the motility of the cloned micro-organisms in response to theophylline in a dose-dependent manner (FIG. 2B). The results are shown in motility plates 208 and 210.

Example 3

The library screening method described above for constructing synthetic riboswitches is applied to the lacI gene. LacI protein is a well known repressor of lacZ, and therefore the expression of the lacI gene, like the crp gene, can be detected on X-gal plates. A lacI-lacZ translational fusion on the chromosome of an *E. coli* MG1655 lacZ null mutant was constructed to illustrate that the library screening on X-gal plates allows for detection of riboswitches for any target genes as long as lacZ is fused to them.

Figure 3:
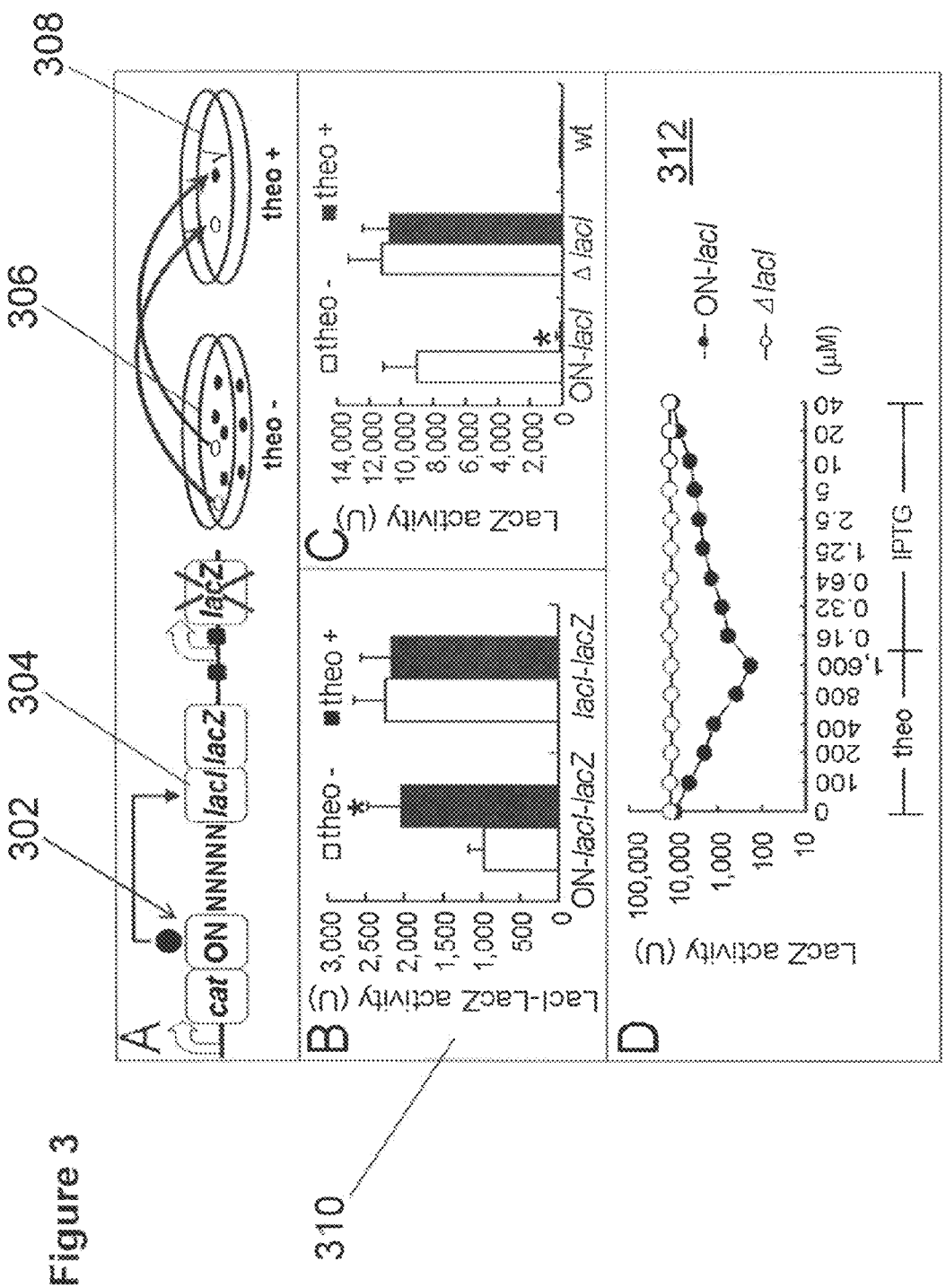
FIG. 3A is a schematic illustration of the construction of an ON-riboswitch for the lacI gene using a library-screening method, in accordance with one embodiment.
FIG. 3B is a graph showing the regulatory effect of the ON-lacI riboswitch on the lacI expression in the lacI-lacZ mutant strain of *E. coli* MG1655, in accordance with one embodiment.
FIG. 3C is a graph showing the indirect regulatory effect of the ON-lacI riboswitch modulated by LacI on lacZ expression, in accordance with one embodiment.
FIG. 3D is a graph showing two-way, tunable control of a target gene (i.e. lacZ) mediated by the combination of an ON-lacI riboswitch and LacI-binding sites, in accordance with one embodiment.

The loxP-cat-loxP selectable cassette was inserted immediately after the stop codon of the lacZ gene on the MG1655 chromosome using recombineering methods. Next, the lacZ-loxP-cat-loxP cassette was PCR amplified and inserted (in frame) immediately prior to the stop codon of the target gene on the chromosome. The inserted lacZ fragment started from the 8th codon of the lacZ gene, and was co-transcribed and translated with the fused genes. The expression of gene-lacZ fusions was quantified using a β-galactosidase assay. Levels of β-galactosidase were calculated using the following formula:

units $(U) = 00420 \times 1000 / (00600 \times \text{hydrolysis time} \times \text{volume of lysate})$ To engineer an ON-riboswitch of the lacI gene, riboswitch cassette 302, cat-aptamer-linker-random sequence, was integrated upstream of the ribosomal binding site of lacI-lacZ usion 304 on the chromosome using standard recombineering methods (FIG. 3A).

The resulting mutant collection was grown on X-gal plates 306 in the absence of theophylline. Approximately 2000 colonies were screened for color. Two white clones were identified. Both clones turned blue when grown on X-gal plates 308 in the presence of theophylline, indicating that they contained a theophylline sensitive ON-riboswitch 302 (ON-lac/). The clones were sequenced and their random sequence was revealed to be TGTAT (UGUAU) and CGTAT (CGUAU), respectively. The riboswitch carrying TGTAT (UGUAU- 402—FIG. 4A) is referred to as ON1-lacI and the riboswitch carrying CGTAT (CGUAU-406—FIG. 4B) is referred to as ON2-lacI The effectiveness of ON1-lacI carrying the TGTAT sequence of lacI was confirmed using a β-galactosidase assay comparing lacI-lacZ fusion 304 levels with and without theophylline (graph 310, FIG. 3B).

The successful application of the library screeening-based method for constructing riboswitches for the crp and lacI genes demonstrate that this method is not confined to a specific gene, but is an extensible method, applicable to many gene loci.

Secondary structures of the ON and OFF riboswitches of lacI were then predicted using RNAstructure 5.1 software program (University of Rochester Medical Center, Rochester, N.Y.). The secondary structure prediction of all the riboswitches was performed for a 237-nt long fragment starting with a 33nt-stem-loop structure (−136 nt relative to the translational start site) and ending at the 100th nucleotide of lacI. For each riboswitch, the optimal structure with the minimum free energy was chosen for structural analysis. To predict riboswitch structures in the ligand-bound form, we utilized the 'force pair' function of the RNAstructure 5.1 program to force the theophylline binding pocket to form.

Figure 4:
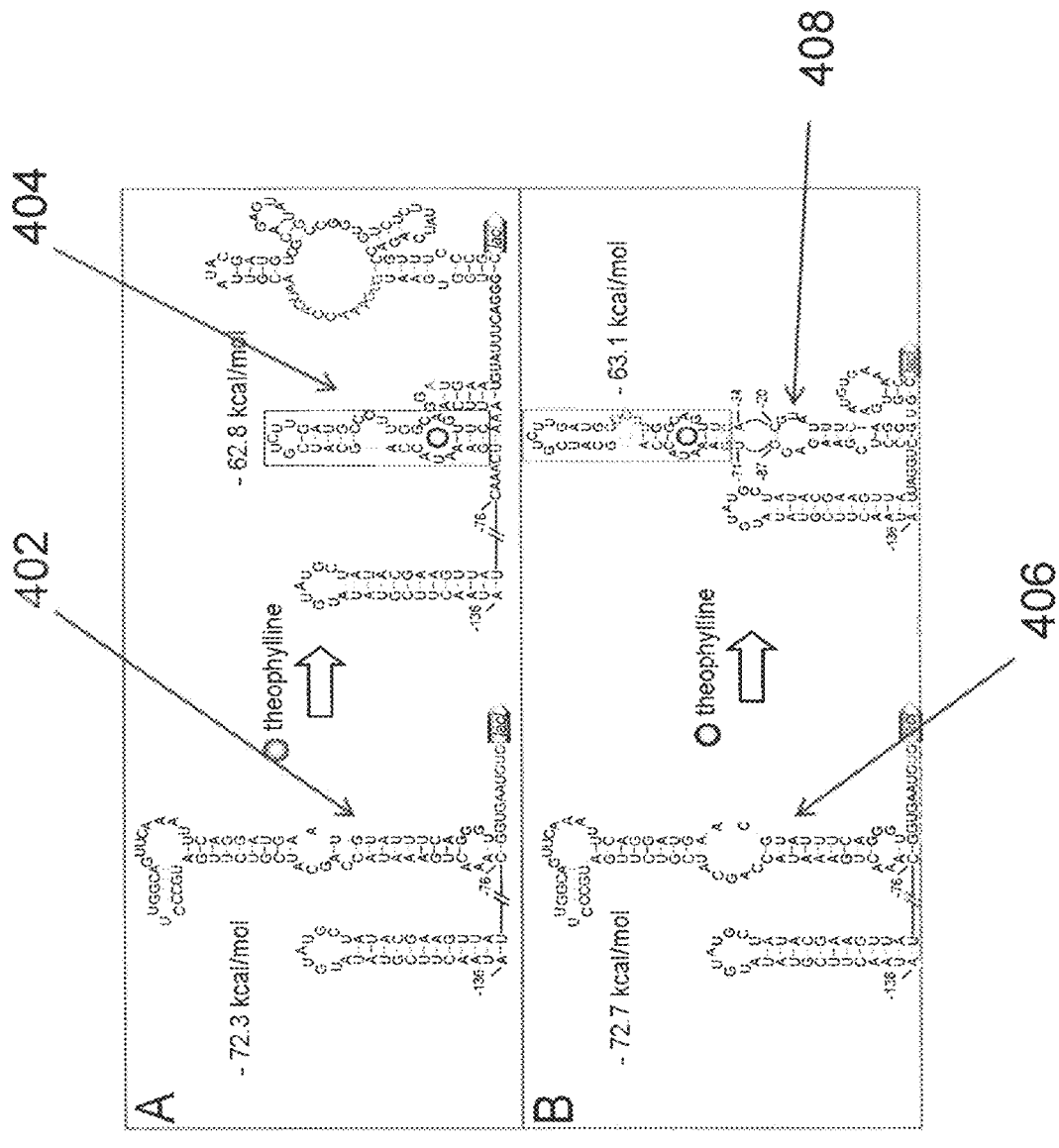
Figure 5:
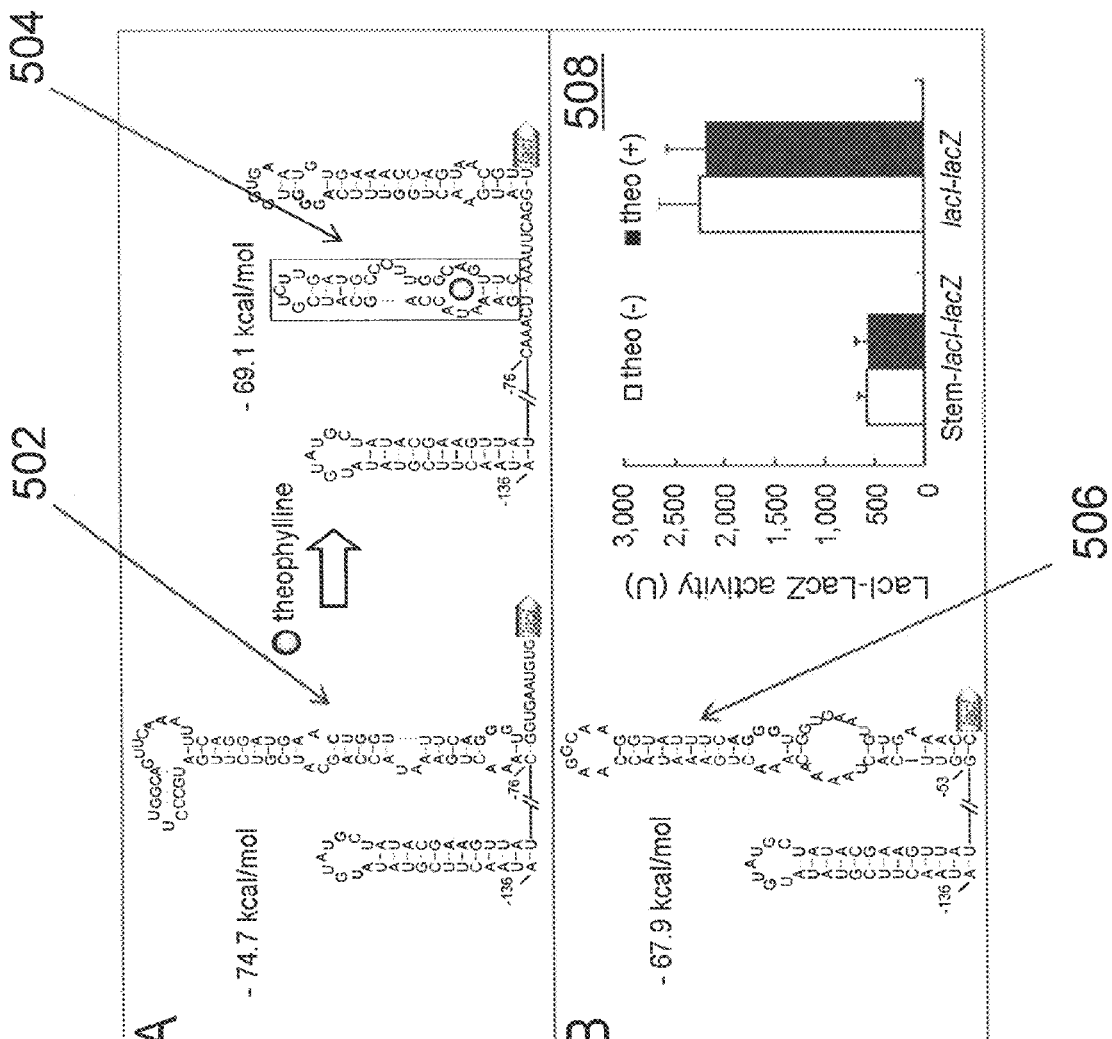

The structure analysis revealed that ON1-lacI in the non-ligand-bound state forms a 9 bp-stem 402 immediately adjacent to the RBS (FIG. 4A). Stem 402 exists in not only the optimal structure but also alternative structures with higher free energy (data not shown). Except for the first nucleotide, the random sequence contributes to the formation of stem 402. When theophylline binds to the riboswitch, the conformation changes and long stem 402 adjacent to the RBS does not form (FIG. 4A), but instead is replaced by structure 404. In ON2-lacI, a similar stem structure 406 was found (FIG. 4B). When theophylline binds to riboswitch ON2-lacI structure 408 forms in place of stem structure 406. Interestingly, the 5 nt-random sequences of the two ON riboswitches share the latter four nucleotides, which is unlikely to be coincident. We proposed that the latter four nucleotides GUAU (406—FIG. 4B) is critical for the action of ON1-lacI and ON2-lacI by being part of the long stem immediately upstream of the RBS. If this is true, then the riboswitch OFF-lacI in the absence of theophylline would not contain a long stem next to the RBS, allowing for the gene translation; but would form the stem structure when bound by the ligand, repressing the expression. As shown in FIG. 5A, the predicted structures of OFF-lacI in the presence (504) and in the absence (502) of theophylline are totally in agreement with this hypothesis. See also 5 nucleotide stretch CUGGU (CTGGT). According to the prediction of free energy using RNA structure 5.1, all the structures in the non-bound state have lower free energy than the structures in the ligand-bound state (FIGS. 4, 5), and therefore are proposed to predominate in the absence of theophylline. Only when theophylline binds to the riboswitches, would the equilibrium distribution be shifted to the formation of structures with a theophylline-binding pocket, switching ON or OFF the target. To confirm the role of a long stem adjacent to RBS in the riboswitch-mediated gene control, we integrated a long stem (10 nt)-loop structure immediately upstream of the RBS of lacI fused with lacZ (FIG. 5B). In the resulting mutant named Stem-lacI-lacZ the expression levels of the lacI-lacZ fusion were reduced by 74% (shown in graph 508, FIG. 5B) as a result of the insertion of long stem 506 (FIG. 5B). Taken together, the synthetic riboswitches regulate lacI expression by forming or disrupting a long stem (9-10 nt) immediately upstream of the RBS in response to theophylline.

The riboswitches described above perform either an ON or OFF function, but not both, and thus are 'one-way' switches. These riboswitches substantially inhibit translation of the target genes in the OFF-state and increase translation in the ON-state. However, neither complete repression of translation in the OFF-state, nor wild-type levels of translation in the ON-state are achieved (FIG. 1C, FIG. 3B). Nevertheless, the riboswitches fine-tune expression of their target genes in response to the theophylline concentration in the host bacterial culture, and modulate the corresponding biological behavior (motility) of the host organism.

Riboswitches known in the prior art lack portability because riboswitch function is significantly affected by flanking sequences so that an active riboswitch of a gene becomes inert when assembled with another gene. This limitation is overcome in one embodiment by combining ON-lacI riboswitch 302 with the LacI protein and LacI binding site (LacIbs) to construct a two-way system.

LacI is a transcriptional repressor protein that inhibits transcription of the lacZ gene by binding to two LacIbs upstream of lacZ. An *E. coli* mutant containing ON-lacI riboswitch 302 displayed high basal levels of LacI expression in the absence of the ligand (theophylline) and had only a one fold-increase in LacI levels in the presence of the ligand (FIG. 3B). However, the narrow dynamic range of ON-lacI riboswitch 302 is magnified when the LacI repressor controls its downstream target.

Example 4

ON-lacI riboswitch 302 was incorporated into the chromosome upstream from intact lad gene (i.e., not fused with lacZ). The LacI protein represses expression of lacZ so that ON riboswitch 302 indirectly switches off lacZ in response to theophylline. ON-lacI 302, when combined with LacIbs (upstream from lacZ) displayed partial repression of lacZ in the absence of theophylline, but almost completely repressed lacZ expression in the presence of theophylline (FIG. 3C). Thus, LacI represson protein functions as an intermediary modulator and significantly improves the performance of ON-lacI riboswitch 302.

ON-lacI riboswitch 302 makes two-way gene regulation possible because the Lad repressor protein can be inactivated by isopropyl β-D-1-thiogalactopyranoside (IPTG). Thus, adding theophylline to the culture medium switches on lacI translation, and transcriptionally represses the target genes of LacI. In contrast. IPTG inactivates LacI by binding to the protein and derepresses transcription of the target genes.

Two-way control was verified by determining β-galactosidase levels of the cells carrying both ON-lacI riboswitch 302 and an intact lacZ gene locus. Theophylline and IPTG regulated lacZ in opposite directions in a concentration-dependent manner (graph 312, FIG. 3D). The effective concentration range of theophylline was 100-1600 µM. Theophylline concentrations less than 100 µM resulted in little regulation and those higher than this range failed to cause additional repression indicating saturation. When IPTG was added to the medium containing 1600 µM theophylline, lacZ was derepressed. The effective range of IPTG was 0.16-40 µM.

Inducible gene control based on binding of LacI repressor protein to LacIbs (binding sites) has been widely used for various non-lacZ genes in prokaryotic and eukaryotic cells, indicating that the inducibility of LacI-responsive promoters are less likely to be affected by downstream targets. Thus, ON-lacI riboswitch 302 is capable of regulating any target gene preceded by LacIbs when using LacI as a portable modulator. ON-lacI riboswitch 302 in combination with the LacI protein and LacIbs (ON-lacI-LacIbs) acts as a magnified, tunable, two-way and portable device for gene control. The ON-lacI-LacIbs device is as short as 2500 bp, and therefore can be easily PCR amplified and integrated into target genes.

RpoS is an alternative sigma factor of RNA polymerase, governing expression of over 200 genes, and having a critical role in the survival micro-organisms in the presence of a number of stresses including acid shock, osmotic stress, heat shock, oxidative damage, and starvation. RpoS negatively regulates *Salmonella* virulence and has, therefore, been mutated to engineer live attenuated vaccine strains. Given the significance of RpoS as a global response regulator and its potential medical use, it is desirable that the rpoS gene be placed under the control of the ON-lacI-LacIbs riboswitch device for tunable and two-way expression control.

Example 5

The ON-lacI-LacIbs cassette (2500 bp) from the genome of the strain carrying the ON riboswitch of lacI is amplified using semi-quantitative reverse transcriptase PCR methods. Cassette 602 is composed of the cat gene, the ON-lacI riboswitch, the lacI gene, and the lacI-lacZ intergenic region containing two LacIbs. The cat gene facilitates integration of this cassette immediately upstream of any target gene via recombineering. The riboswitch cassette was inserted upstream of the ribosomal binding site of rpoS gene locus 406 (FIG. 6A). Next, the native lacI was deleted from this strain, generating a new mutant strain, ON-lacI-rpoS. This strain was used to test whether rpoS gene locus 606 could be controlled by the theophylline-responsive and LacI-repressible regulation cassette 602. Since rpoS is required for acid resistance, survival of strain 602 under acidic conditions was assayed. Overnight cultures were treated with acid (pH 2.0) for 2 hours, and then serially diluted in neutral medium. After culturing overnight, colony forming units (CFU) of acid-treated and untreated cells were determined Acid survival (%) was calculated using the formula: Acid survival (%)=100× (CFU of treated/CFU of untreated).

That expression of rpoS turned on in the absence of theophylline was indicated by a survival percentage of a mutant strain containing cassette 602 that was comparable to the wild-type strain after 2 hour acid treatment (pH 2.0), as shown in graph 610, FIG. 6B. The switch turned off lacI 604 in the absence of theophylline and therefore, rpoS gene locus 606 was in the ON-state. When theophylline was added, the cells became sensitive to acid (FIG. 6B), providing evidence that the addition of theophylline turned on the expression of lacI 604 and the latter repressed the expression of rpoS gene locus 606. Acid survival in the absence of theophylline was approximately the same as the wild-type levels, and decreased with increasing concentrations of theophylline (curve 608, FIG. 6B). Acid survival reached minimum 612 that was comparable to that of an rpoS null mutant *E. coli* strain when theophylline was increased to 1600 μM. Increasing concentrations of IPTG added to the medium containing 1600 μM theophylline caused a corresponding increase in the acid survival 614, and was restored to the wild-type levels 616 in the presence of 40 μM IPTG, consistent with the response curve of the ON-lacI strain. These data for rpoS gene locus 604 not only confirmed the portability, tenability and two-way control features of ON-lacI-LacIbs 602 device, but also suggested the potential utility of this device in flexibly manipulating virulence and immunogenicity of live vaccines and bacteria for other medical purposes.

Naturally existing, small, noncoding RNA CsrB is well known as an antagonist of the CsrA protein. It has previously been demonstrated that noncoding RNA CsrB promotes cellular autoaggregation and biofilm formation by indirectly activating the expression of the pgaABCD operon via CsrA protein.

CsrB-overproducing cells were coupled with ON-lacI riboswitch 302 device to control pga operon 702 and demonstrate trans-acting regulation of expression of a target gene (FIG. 7A). CsrB locus 706 has previously been cloned into a high copy vector (plasmid) 704. Two LacIbs 112 were inserted around the transcriptional start site to place expression of CsrB locus 706 under the control of ON-lacI riboswitch 302. Since one LacIb is after the transcriptional start site, the resulting CsrB differs slightly from the native one by the extra 21 nt-sequence (i.e. LacIb). Expression of CsrB locus 706 was induced by IPTG and autoaggregation (which serves as an indicator of CsrB expression) occurred (data not shown), indicating that CsrB locus 706 is functional. This CsrB-carrying vector 704 was introduced into the ON-lacI strain, and autoaggregation and biofilm formation were examined.

To measure autoaggregation, overnight cultures were diluted 1:500 and incubated at 37° C., with shaking at 220 rpm, in liquid LB medium. When cells aggregated (visualized macroscopically by the clumping or 'fluffing' of cells in liquid cultures), 100 μl of each cell suspension was transferred to flat-bottom 96-well plates (Iwaki, Tokyo, Japan) and the images of the cell aggregates were captured by scanning. To better visualize the cell aggregates, 1 μl of crystal violet (0.1%) was added to each cell suspension immediately prior to image capture. Cellular autoaggregation was also examined microscopically. Cell suspensions were spread on a microscope slide, heat-fixed, stained with DAPI (4'6-diamidino-2-phenylindol), and imaged using a fluorescence stereomicroscope SZX12 (Olympus, Tokyo, Japan) with DAPI filter sets.

Biofilms were formed on polystyrene, flat-bottom 96-well microtiter plates (Iwaki, Tokyo, Japan). 200 μl of each cell suspension ($10^5$ cells/ml) was transferred into each well of a microtiter plate, and incubated for 24 h at 37° C. in a shaker at 75 rpm. Resulting biofilms were washed thrice with PBS and air dried. Then, biofilms were stained with 100 ml of 0.4% aqueous crystal violet solution for 15 min. Next, biofilms were washed three times with sterile distilled water and immediately destained with 200 μl of 95% ethanol. After 30 min of destaining, 100 μl of destaining solution was transferred to a new well and measured with a microtiter plate reader (SpectraMAX®340 Tunable Microplate Reader; Molecular Devices Ltd.) at 595 nm.

In the absence of theophylline, LacI levels are low and CsrB 706 expression is turned on (FIG. 7A). As predicted, the cells autoaggregated and formed high levels of biofilms, showing that the pga 702 expression was induced due to the overproduction of CsrB protein, shown in scans 710 and graph 712 (FIG. 7B-C). In the presence of theophylline, lacI expression is turned on and CsrB production is repressed by LacI repressor protein. The repression of CsrB locus 706 results in upregulation of CsrA 708, which, in turn, inhibits autoaggregation and biofilm formation (FIG. 7A). Consequently, the cells are negative with respect to autoaggregation and form low levels of biofilms (FIG. 7B-C). When IPTG is added together with theophylline, the activity of LacI repressor protein is inhibited, and CsrB is formed at high levels (FIG. 7A). As a result, autoaggregation and biofilm formation are restored in the presence of IPTG and theophylline (FIG. 7B-C).

The changes in expression of CsrB locus 706 in response to theophylline and IPTG were confirmed by semi-quantitative reverse transcription polymerase chain reaction methods (RT-PCR). Total RNA was isolated from overnight cultures in LB medium. Subsequently, 2 μg of RNA was reverse transcribed in a total reaction volume of 20 μl using the ThermoScript RT-PCR system (Invitrogen). Each reaction was incubated at 55° C. for 50 min followed by 15 min at 70° C. 2 μl of the resulting reverse transcript products (cDNA) were then used for 18, 20, 22 and 24 rounds of PCR (30s each at 94° C., 55° C., and 72° C.) with Ex Tag DNA polymerase (Takara Bio Inc.) and primers complementary to csrB (RT-CsrB-F: 5'-GT-CAGACAACGAAGTGAACATCAGG-3' (SEQ ID NO: 3) and RT-CsrB-R: 5'-GGAGCACTGTATTCACAGCGCT-3' (SEQ ID NO: 4)) and the 16S rRNA gene (RT-16S-F: 5'-CTC-CTACGGGAGGCAGCAG-3' (SEQ ID NO: 5) and RT-16S-R: 5'-CTCCGTATTACCGCGGCTG-3' (SEQ ID NO: 6)) to co-amplify the gene of interest and the internal control. PCR products were separated on 1.5% agarose gel 714.

These results (FIG. 7D) demonstrate that ON-lacI riboswitch 302 can be used in combination with a small noncoding RNA to exert trans-acting control of target expression, alleviating the need for modification of the chromosome and expanding the applications of this riboswitch system.

Bacterial cells switch from rapid growth during which they produce and excrete acetate (dissimilation) in the presence of abundant nutrients to slower growth supported by the import and utilization of the excreted acetate (assimilation) when glucose is exhausted. This physiological event is defined as an acetate switch, a survival response allowing cells to compete successfully during carbon starvation. It was previously reported that RpoS positively regulates consumption of acetate by activating the expression of acetyl-coenzyme A synthetase enzyme (Acs). However, the opposite results were obtained with ON-lacI-rpoS construction provided herein. When ON-lacI-rpoS was in the ON-state, and in the absence of both theophylline and IPTG, the ON-lacI-rpoS cells exhibit acetate assimilation similar to that of the wild type strain, shown in graph 602 (FIG. 8A). When grown in the presence of theophylline (2 mM) and absence of IPTG, rpoS expression was shut off and accordingly, acetate assimilation was accelerated (FIG. 8A). When IPTG (1 mM) was added to the medium to derepress rpoS gene locus 606 expression, the acetate assimilation was restored to the wild-type levels (FIG. 8A). Neither theophylline nor IPTG had any effect on acetate assimilation in the wild type strain (data not shown), eliminating a possible nonspecific effect of the two chemicals. The enhanced acetate assimilation was also observed with the newly constructed rpoS gene locus null mutant, shown in graph 804 (FIG. 8B). All the cell suspensions were adjusted to an OD of 0.08 prior to the acetate assays, and cells with varying RpoS activities showed comparable cell growth rates (data not shown), ruling out any possible effects of growth rate on acetate assimilation. It is therefore apparent that RpoS represses acetate assimilation.

Acetate assimilation depends on the acetyl-GoA synthetase (Acs) and the phosphotransacetylase (Pta)-acetate kinase (AckA) pathways, 806 (FIG. 8C). It therefore seemed probable that RpoS inhibited the Acs and/or the Pta-AckA pathway, and that deleting rpoS would increase their expression levels. Accordingly, cells were incubated for 6 h under conditions of acetate assimilation and then examined for the possible effects of RpoS on the levels of Acs and AckA-Pta. B-galactosidase data indicates that the removal of rpoS gene locus 606 slightly reduces the expression of an acs-lacZ translational fusion on the chromosome, graph 808 (FIG. 8D). However, deleting rpoS gene locus 606 resulted in a 5-fold increase in the expression levels of an ackA-lacZ translational fusion (FIG. 8D). The pta and ackA loci are in the same operon. The ackA-lacZ data revealed that the Pta-AckA pathway was enhanced in both the rpoS null mutant and the theophylline-grown ON-lacI-rpoS cells, relative to the wild type. It therefore follows that the increased acetate assimilation as a result of repression of rpoS gene locus 606 or deletion (ON-lacI-rpoS in the presence of theophylline), is at least partially due to the elevated activity of the Pta-AckA pathway.

It is notable that these results on the role of RpoS in acetate assimilation are the opposite of those of previous studies using rpoS mutants. rpoS mutants frequently generate secondary mutations within the hns gene (encoding H-NS, an abundant nucleoid-associated protein) to compensate for the loss of RpoS function. It is therefore likely that rpoS mutants used in those studies have accumulated analogous compensatory mutations and consequently exhibited the opposite phenotype. If this is true, then cells deleted for hns, compared to the wild type, should have a reduced ability to scavenge for extracellular acetate. As predicted, removing hns inhibited acetate assimilation as revealed by sustained high levels of extracellular acetate (FIG. 8B), supporting the notion that the previous observations with the rpoS mutants may result from compensatory mutations in hns.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

The invention claimed is:

1. A gene expression control device comprising:
   a chloramphenicol resistance gene, linked in 5' to 3' orientation to a theophylline-specific aptamer fragment;
   the 3' end of the theophylline-specific aptamer fragment linked to the 5' end of a linker portion and a 5-nt random sequence, in 5' to 3' orientation;
   a lacI gene preceded by its native ribosome binding site; and
   a native lacI-lacZ intergenic region containing four lac promoters and two LacIbs, wherein when the control device is inserted into the genome of *E. coli* MG1655 upstream from a translational start site of a target gene, the transcription rate of the target gene is controlled by theophylline binding to the aptamer fragment.

2. The device of claim 1 wherein the 5-nt random sequence is TGTAT, in a 5' to 3' orientation.

3. The device of claim 1 wherein the target gene is selected from the group consisting of a lacZ gene locus, a rpoS gene locus, and a csrB gene locus.

4. A gene expression construct comprising a chloramphenicol resistance gene, a theophylline-specific aptamer fragment, a linker portion and a 5-nt random sequence, in 5' to 3' orientation, a lacI gene and two LacIbs (binding sites), wherein when the construct is inserted into the genome of *E. coli* MG1655 in a position 5' to the ribosome binding site of a target gene, transcription of a target gene is controlled by theophylline binding to the aptamer fragment, and transcription of the target gene is detected using standard assay methodology.

* * * * *